United States Patent
Huang et al.

(10) Patent No.: US 7,015,047 B2
(45) Date of Patent: Mar. 21, 2006

(54) MICRODEVICES HAVING A PREFERENTIAL AXIS OF MAGNETIZATION AND USES THEREOF

(75) Inventors: Mingxian Huang, San Diego, CA (US); Lei Wu, San Diego, CA (US); Xiaobo Wang, San Diego, CA (US); Junquan Xu, San Diego, CA (US); Guo Liang Tao, San Diego, CA (US); David M. Rothwarf, La Jolla, CA (US)

(73) Assignee: Aviva Biosciences Corporation, San Diego, CA (US)

( * ) Notice: Subject to any disclaimer, the term of this patent is extended or adjusted under 35 U.S.C. 154(b) by 207 days.

(21) Appl. No.: 10/104,571

(22) Filed: Mar. 21, 2002

(65) Prior Publication Data

US 2002/0187501 A1    Dec. 12, 2002

Related U.S. Application Data

(63) Continuation-in-part of application No. 09/924,428, filed on Aug. 7, 2001.

(60) Provisional application No. 60/264,458, filed on Jan. 26, 2001.

(30) Foreign Application Priority Data

Feb. 23, 2001    (CN) ............................... 01104318 A

(51) Int. Cl.
    *G01N 33/553*    (2006.01)
(52) U.S. Cl. ............................. 436/526; 435/7.1; 435/6
(58) Field of Classification Search .................... 435/4, 435/6, 7.1, 7.7, 287.3, 287.8, 287.9, 288.1, 435/288.2, 288.3, 288.4, 288.5, 288.6, 288.7; 436/518, 525, 526, 534, 538, 541, 546; 422/50, 422/55, 56, 57, 58, 68.1, 82.05, 82.07
See application file for complete search history.

(56) References Cited

U.S. PATENT DOCUMENTS

| | | | |
|---|---|---|---|
| 2,797,149 A | 6/1957 | Skeggs | |
| 3,109,719 A | 11/1963 | Eckert | |
| 4,053,433 A | 10/1977 | Lee | ............................. 252/408 |
| 4,390,452 A | 6/1983 | Stevens | .................... 252/408.1 |
| 5,120,662 A | 6/1992 | Chan et al. | .................. 436/530 |
| 5,132,097 A | 7/1992 | Van Deusen et al. | |
| 5,508,200 A | 4/1996 | Tiffany et al. | ................. 436/44 |
| 5,651,900 A | 7/1997 | Keller et al. | ................... 216/56 |
| 5,660,680 A | 8/1997 | Keller | ........................... 438/50 |
| 5,736,330 A | 4/1998 | Fulton | ............................. 435/6 |

(Continued)

FOREIGN PATENT DOCUMENTS

EP           0629989         12/1994

(Continued)

OTHER PUBLICATIONS

U.S. Appl. No. 09/636,104, filed Aug. 10, 2000, Wang et al.

(Continued)

*Primary Examiner*—Long V. Le
*Assistant Examiner*—Ann Y. Lam
(74) *Attorney, Agent, or Firm*—Morrison & Foerster LLP

(57) ABSTRACT

This invention relates generally to the field of moiety or molecule isolation, detection and manipulation and library synthesis. In particular, the invention provides a microdevice, which microdevice comprises: a) a magnetizable substance; and b) a photorecognizable coding pattern, wherein said microdevice has a preferential axis of magnetization. Systems and methods for isolating, detecting and manipulating moieties and synthesizing libraries using the microdevices are also provided.

45 Claims, 8 Drawing Sheets

U.S. PATENT DOCUMENTS

| | | | |
|---|---|---|---|
| 5,893,974 A | 4/1999 | Keller et al. ............... | 210/483 |
| 5,942,407 A | 8/1999 | Liotta et al. ................. | 435/28 |
| 5,981,180 A | 11/1999 | Chandler et al. ............. | 435/6 |
| 5,985,543 A | 11/1999 | Siegel | |
| 5,998,224 A * | 12/1999 | Rohr et al. ................. | 436/526 |
| 6,029,518 A | 2/2000 | Oeftering ................... | 73/570.5 |
| 6,048,698 A | 4/2000 | Eaton et al. .................... | 435/6 |
| 6,057,107 A | 5/2000 | Fulton .......................... | 435/6 |
| 6,096,496 A * | 8/2000 | Frankel ........................ | 435/4 |
| 6,114,038 A * | 9/2000 | Castro et al. .......... | 428/402.24 |
| 6,127,132 A | 10/2000 | Breitling et al. ............. | 435/7.1 |
| 6,174,708 B1 | 1/2001 | Sodoyer et al. ............ | 435/91.1 |
| 6,180,351 B1 | 1/2001 | Cattell ........................... | 435/6 |
| 6,214,560 B1 | 4/2001 | Yguerabide et al. ......... | 435/7.1 |
| 6,252,664 B1 | 6/2001 | Barbera-Guillem ......... | 356/417 |
| 6,361,749 B1 * | 3/2002 | Terstappen et al. .... | 422/186.01 |
| 6,548,264 B1 * | 4/2003 | Tan et al. .................. | 435/7.21 |

FOREIGN PATENT DOCUMENTS

| | | |
|---|---|---|
| GB | 1568699 | 6/1980 |
| GB | 2289150 | 11/1995 |
| GB | 2306484 | 5/1997 |
| JP | 05240869 | 9/1993 |
| WO | WO 96/39937 | 12/1996 |
| WO | WO97/40385 | 10/1997 |
| WO | WO 99/47254 | 9/1999 |
| WO | WO 00/16893 | 5/2000 |
| WO | WO 00/54882 | 9/2000 |
| WO | WO 02/27909 | 4/2002 |
| WO | WO 02/31505 | 4/2002 |

OTHER PUBLICATIONS

U.S. Appl. No. 09/679,024, filed Oct. 4, 2000, Wang et al.
U.S. Appl. No. 09/924,428, filed Augl. 7, 2001, Wu et al.
Ahn et al., J. of Microelectromechanical Systems (1996) 5:151-157.
Anonymous, "Light-Emitting Chips Speed Up Drug Discovery" Chemical Engineering (2000) 107(10):23.
Ashkin, Biophys. J. (1992) 61:569-582.
Bart et al., Sensors and Acuators (1988) 14:269-292.
Becker et al., Proc. Natl. Acad. Sci. (1995) 92:860-864.
Blanchard et al., Biosensors Bioelectronics (1996) 6/7:687-690.
Bleaney, B.I. and Bleaney, B., *Electricity an Magnetism* Oxford, pp. 169-174, 519-524 (1975).
Block, Nature (1992) 360:493-496.
Bruchez, Jr. et al., Science (1998) 281:2013-2015.
Chan and Nie, Science (1998) 281:2016-2018.
Chu, Science (1991) 253:861-866.
Dolle, Journal of Combinatorial Chemistry (2000) 2:383-433.
Ferguson et al., Anal. Chem. (2000) 72:5618-5624.
Fodor et al., Science (1991) 251:767-773.
Fuhr et al., Sensors and Materials 7:131-146.
Hagedorn et al., Journal of Electrostatics (1994)33:159-185.
Han et al., Nature Biotechnology (2001) 19:631-635.
Huang et al., J. Phys. D.: Appl. Phys. (1993) 26:1528-1535.
Kronick, in Methods of Cell Separation, vol. 3, Catsimpoolas (ed.) (1980) pp. 115-139.
Lam et al., Chem. Rev. (1997) 97:411-448.
Mc Gall et al., J. Am. Chem. Soc. (1997) 119:5081-5090.
Nicewarner-Peña et al., Science (2001) 294(5540):137-41.
Oliver et al., Clinical Chemistry (1998) 44:2057-2060.
Safarik and Safarikova, J. of Chromatography (1999) 722 (B):33-53.
Schena et al., Science (1995) 270:467-470.
Singh-Gasson et al., Nature Biotechnology 17:974-978 (1999).
Terrett, N., "Encoded Combinatorial Synthesis" Chapter 5 *In Combinatorial Chemistry* Oxford University Press pp. 46-94 (1998).
Vignali, J. Immunol. Methods (2000) 243:243-255.
Wang et al., Biochim. Biophys. Acta (1995) 1243:185-194.
Wang et al., Biophys. J. (1997) 72:1887-1899.
Wang et al., IEEE Transaction on Industry Applications (1997) 33(3):660-669.
Wang et al., Science (1998) 280:1077-1082.
Wright et al., IEEE J. of Quantum Electronics (1990) 26:2148-2157.
Yasuda et al., Jpn. J. Appl. Physics (1996) 35:3295-3299.
Yoshioka and Kawashima, Acustica (1995) 5:167-173.
Zammatteo et al., Anal. Biochem. (2000) 280:143-150.

* cited by examiner

MICRODEVICES HAVING A PREFERENTIAL AXIS OF MAGNETIZATION AND USES THEREOF

The present application is a continuation-in-part of U.S. patent application Ser. No. 09/924,428, filed Aug. 7, 2001, now pending, which claims priority of U.S. Provisional Patent Application Ser. No. 60/264,458, filed Jan. 26, 2001 and Chinese Patent Application Serial No. 01104318.0, filed Feb. 23, 2001. The contents of the above Patent Applications are incorporated by reference herein in their entireties.

TECHNICAL FIELD

This invention relates generally to the field of moiety or molecule isolation, detection, manipulation and synthesis. In particular, the invention provides a microdevice, which microdevice comprises: a) a magnetizable substance; and b) a photorecognizable coding pattern, wherein said microdevice has a preferential axis of magnetization. Systems and methods for isolating, detecting, manipulating and synthesizing moieties using the microdevices are also provided.

BACKGROUND ART

High-density, high throughput biological and biochemical assays have become essential tools for diagnostic and research applications, particularly in areas involving the acquisition and analysis of genetic information. These assays typically involve the use of solid substrates. Examples of typical quantitative assays performed on solid substrates include measurement of an antigen by ELISA or the determination of mRNA levels by hybridization. Solid substrates can take any form though typically they fall into two categories—those using spherical beads or those using planar arrays.

Planar objects such as slide- or chip-based arrays offer the advantage of allowing capture molecules, e.g., antibody or cDNA, of known identity to be bound at spatially distinct positions. Surfaces are easily washed to remove unbound material. A single mixture of analytes can be captured on a surface and detected using a common marker, e.g., fluorescent dye. The identification of captured analytes is governed by the spatial position of the bound capture molecule. Archival storage of the array is generally possible. Because the array corresponds to a stationary flat surface, detection devices are generally simpler in design and have lower cost of manufacture than bead reading devices. One of the difficulties of the planar array approach is the initial positioning of the capture molecule onto the surface. Techniques such as robotic deposition (e.g., "Quantitative monitoring of gene expression patterns with a complementary DNA microarray" by Schena et al. *Science*, 270:467–470 (1995)), photolithography (e.g., "Light-directed, spatially addressable parallel chemical synthesis" by Fodor et. al. *Science*, 251:767–773 (1991)), or ink-jet technologies (e.g., "High-density oligonucleotide arrays" by Blanchard et al. *Biosensors Bioelectronics*, 6/7:687–690 (1996)) are generally used. These methods have a number of limitations. They require expensive instrumentation to generate high density arrays (greater than 1000 features/cm$^2$), and there is no ability to alter the pattern after manufacture, e.g., replace one capture cDNA with another, consequently any alterations require a new manufacturing process and greatly increase expenses. Moreover, molecules bound to large flat surfaces exhibit less favorable reaction kinetics than do molecules that are free in solution.

One way around many of these problems is to use surfaces of small particles. Spherical beads have been the small particles of choice because of their uniform symmetry and their minimal self-interacting surface. Small particles, however, suffer from the problem of being difficult to distinguish, e.g., a mixture of beads is not spatially distinct. A number of technologies have been developed to overcome this problem by encoding beads to make them distinguishable. Companies such as the Luminex Corporation have developed methods of doing this by incorporating different mixtures of fluorescent dyes into beads to make them optically distinguishable. In a similar manner, other researchers have developed ways of incorporating other optically distinguishable materials into beads (e.g., "Quantum-dot-tagged microbeads for multiplexed optical coding of biomolecules" by Han et al. *Nature Biotechnology*, 19:631–635 (2001)). Furthermore, quantum dots, nanometer scale particles that are neither small molecules nor bulk solids, have also been used for bead identification. Their composition and small size (a few hundred to a few thousand atoms) give these dots extraordinary optical properties that can be readily customized by changing the size or composition of the dots. Quantum dots absorb light, then quickly re-emit the light but in a different color. The most important property is that the color of quantum dots—both in absorption and emission—can be "tuned" to any chosen wavelength by simply changing their size. Genicon Sciences Corporation (Their "RLS" particles are of nano-sizes and have certain "resonance light scattering (RLS) properties) also developed micro-beads or nano-beads with optically distinguishable properties. However, in using any of these approaches, it is difficult to manufacture more than 1,000 or so different encoded beads.

Beads are also the format of choice in combinatorial chemistry. Using the one-bead/one-compound procedure (also known as the split and mix procedure) (see "The "one-bead-one-compound" combinatorial library method" by Lam et al. *Chem. Rev.,* 97:411–448 (1997)), it is possible to generate huge libraries containing in excess of 10$^8$ different molecules. However, the beads are not distinguishable in any way other than by identifying the compound on a particular bead. Labeled "tea bags" which contain groups of beads displaying the same compound have been used to distinguish beads. Recently, IRORI has extended the tea bag technology to small canisters containing either a radiofrequency transponder or an optically encoded surface. This technology is generally limited to constructing libraries on the order of 10,000 compounds, a single canister occupies ~0.25 mL. Moreover, the technology is not well suited to high-throughput-screening. PharmaSeq, Inc. uses individual substrates containing transponders. These devices are 250$\mu$×250$\mu$×100$\mu$. Larger libraries can be synthesized directly onto a surface to form planar arrays using photolithographic methods (such as those used by Affymetrix). However, such techniques have largely been restricted to short oligonucleotides due to cost considerations and the lower repetitive yields associated with photochemical synthesis procedures (see e.g., "The efficiency of light-directed synthesis of DNA arrays on glass substrates" by McGall et al. *J. Am. Chem. Soc.*, 119:5081–5090 (1997)). In addition, the available number of photo-labile protecting groups is severely limited compared to the tremendous breadth and diversity of chemically labile protecting groups that have been developed over the past 30+ years for use on beads. Recently, SmartBeads Technologies has introduced microfabricated particles (e.g., strip particles having dimensions of 100$\mu$×10$\mu$×1$\mu$) containing bar codes that can be decoded using a flow-based reader.

Microfabricated particles have the advantage that a nearly infinite number of encoding patterns can be easily incorporated into them. The difficulty lies in being able to easily analyze mixtures of encoded particles. Since such particles tend to be flat objects as opposed to spherical beads, they tend to be more prone to aggregation or overlapping as well as being more difficult to disperse.

Nicewarner-Pena et al., *Science*, 294(5540):137–41 (2001) recently reported synthesis of multimetal microrods intrinsically encoded with submicrometer stripes. According to Nicewarner-Pena et al., complex striping patterns are readily prepared by sequential electrochemical deposition of metal ions into templates with uniformly sized pores. The differential reflectivity of adjacent stripes enables identification of the striping patterns by conventional light microscopy. This readout mechanism does not interfere with the use of fluorescence for detection of analytes bound to particles by affinity capture, as demonstrated by DNA and protein bioassays.

A system incorporating the advantages of planar arrays and of encoded micro-particles would address many of the problems inherent in the existing approaches. Illumina, Inc. has attempted to do this by providing a method of generating arrays of microbeads using etched glass fibers (e.g., "High-density fiber-optic DNA random microsphere array" by Ferguson et al. *Anal. Chem.*, 72:5618–5624 (2000)). However, Illumina's oligonucleotide based fluorescent-encoding microbeads are also limited in the number of unique representations. BioArray Solutions has used Light-controlled Electrokinetic Assembly of Particles near Surfaces (LEAPS) to form arrays of beads on surfaces (WO 97/40385). However, the LEAPS approach is still subject to the same restrictions as bead-based techniques with respect to the types of available encoding.

There exists needs in the art for microdevices and methods that can take the advantages of both microfabricated particles and spatially distinct arrays. This invention address these and other related needs in the art.

DISCLOSURE OF THE INVENTION

In one aspect, the present invention is directed to a microdevice, which microdevice comprises: a) a magnetizable substance; and b) a photorecognizable coding pattern, wherein said microdevice has a preferential axis of magnetization. In a specific embodiment, the present microdevice does not comprise Pt, Pd, Ni, Co, Ag, Cu or Au for encoding purposes. In another specific embodiment, the present microdevice does not comprise Pt, Pd, Ni, Co, Ag, Cu or Au.

In another aspect, the present invention is directed to a system for forming a microdevice array, which system comprises: a) a plurality of the microdevices, each of the microdevices comprising a magnetizable substance and a photorecognizable coding pattern, wherein said microdevices have a preferential axis of magnetization; and b) a microchannel array comprising a plurality of microchannels, said microchannels are sufficiently wide to permit rotation of said microdevices within said microchannels but sufficiently narrow to prevent said microdevices from forming a chain when the major axis of said microdevices is substantially perpendicular to the major axis of said microchannels when the said microdevices are subjected to an applied magnetic field. In a specific embodiment, the microdevice used in the present system does not comprise Pt, Pd, Ni, Co, Ag, Cu or Au for encoding purposes. In another specific embodiment, the microdevice used in the present system does not comprise Pt, Pd, Ni, Co, Ag, Cu or Au.

In still another aspect, the present invention is directed to a method for forming a microdevice array, which method comprises: a) providing a plurality of the microdevices, each of the microdevices comprising a magnetizable substance and a photorecognizable coding pattern, wherein said microdevices have a preferential axis of magnetization; b) providing a microchannel array comprising a plurality of microchannels, said microchannels are sufficiently wide to permit rotation of said microdevices within said microchannels but sufficiently narrow to prevent said microdevices from forming a chain when the major axis of said microdevices is substantially perpendicular to the major axis of said microchannels when the said microdevices are subjected to an applied magnetic field; c) introducing said plurality of microdevices into said plurality of microchannels; and d) rotating said microdevices within said microchannels by a magnetic force, whereby the combined effect of said magnetic force and said preferential axis of magnetization of said microdevices substantially separates said microdevices from each other. In a specific embodiment, the microdevice used in the present method does not comprise Pt, Pd, Ni, Co, Ag, Cu or Au for encoding purposes. In another specific embodiment, the microdevice used in the present system does not comprise Pt, Pd, Ni, Co, Ag, Cu or Au.

In yet another aspect, the present invention is directed to a method for forming a microdevice array, which method comprises: a) providing a plurality of the microdevices, each of the microdevices comprising a magnetizable substance and a photorecognizable coding pattern, wherein said microdevices have a preferential axis of magnetization, on a surface suitable for rotation of said microdevices; and b) rotating said microdevices on said surface by a magnetic force, whereby the combined effect of said magnetic force and said preferential axis of magnetization of said microdevices substantially separates said microdevices from each other. In a specific embodiment, the microdevice used in the present method does not comprise Pt, Pd, Ni, Co, Ag, Cu or Au for encoding purposes. In another specific embodiment, the microdevice used in the present system does not comprise Pt, Pd, Ni, Co, Ag, Cu or Au.

In yet another aspect, the present invention is directed to a method for synthesizing a library, which method comprises: a) providing a plurality of microdevices, each of said microdevices comprises a magnetizable substance and a photorecognizable coding pattern, wherein said microdevices have a preferential axis of magnetization and wherein said photorecognizable coding pattern corresponds to an entity to be synthesized on said microdevice; and b) synthesizing said entities on said microdevices, wherein said microdevices are sorted after each synthesis cycle according to said photorecognizable coding patterns, whereby a library is synthesized, wherein each of said microdevices contains an entity that corresponds to a photorecognizable coding pattern on said microdevice and the sum of said microdevices collectively contains a plurality of entities that is predetermined before the library synthesis. In a specific embodiment, the microdevice used in the present method does not comprise Pt, Pd, Ni, Co, Ag, Cu or Au for encoding purposes. In another specific embodiment, the microdevice used in the present system does not comprise Pt, Pd, Ni, Co, Ag, Cu or Au. A library that is synthesized according to the above method is also provided.

MODES OF CARRYING OUT THE INVENTION

Figure 1:
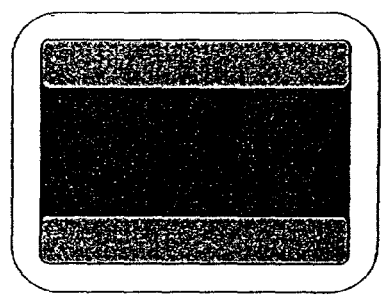
FIG. 1 illustrates an example of a microdevice (Micro-Disk) that is rectangular and consists of four regions. Magnetic bars are shown in light gray. Dark gray region (e.g., made of the material Aluminum, Al) is an encoding region. The surrounding white edge (e.g. made of $SiO_2$) indicates the regions that encapsulate the magnetic bars and encoding region. Arrow indicates direction of the external magnetic field. These different regions are also located separately along the thickness direction. The magnetic bars and the encoding region are located in the middle, and are encapsulated by the top and bottom layers that correspond to the surrounding white edge. In an exemplary microdevice, the MicroDisk contains magnetic bars comprising soft magnetic material, e.g., CoTaZr or NiFe and is $90\mu$ long by $70\mu$ wide by $3.2\mu$ thick.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "magnetic substance" refers to any substance that has the properties of a magnet, pertaining to a magnet or to magnetism, producing, caused by, or operating by means of, magnetism.

As used herein, "magnetizable substance" refers to any substance that has the property of being interacted with the field of a magnet, and hence, when suspended or placed freely in a magnetic field, of inducing magnetization and producing a magnetic moment. Examples of magnetizable substance include, but are not limited to, paramagnetic, ferromagnetic and ferrimagnetic substances.

As used herein, "paramagnetic substance" refers to the substances where the individual atoms, ions or molecules possess a permanent magnetic dipole moment. In the absence of an external magnetic field, the atomic dipoles point in random directions and there is no resultant magnetization of the substances as a whole in any direction. This random orientation is the result of thermal agitation within the substance. When an external magnetic field is applied, the atomic dipoles tend to orient themselves parallel to the field, since this is the state of lower energy than antiparallel position. This gives a net magnetization parallel to the field and a positive contribution to the susceptibility. Further details on "paramagnetic substance" or "paramagnetism" can be found in various literatures, e.g., at Page 169–page 171, Chapter 6, in "Electricity and Magnetism" by B. I Bleaney and B. Bleaney, Oxford, 1975.

As used herein, "ferromagnetic substance" refers to the substances that are distinguished by very large (positive) values of susceptibility, and are dependent on the applied magnetic field strength. In addition, ferromagnetic substances may possess a magnetic moment even in the absence of the applied magnetic field, and the retention of magnetization in zero field is known as "remanence". Further details on "ferromagnetic substance" or "ferromagnetism" can be found in various literatures, e.g., at Page 171–page 174, Chapter 6, in "Electricity and Magnetism" by B. I Bleaney and B. Bleaney, Oxford, 1975.

As used herein, "ferrimagnetic substance" refers to the substances that show spontaneous magnetization, remanence, and other properties similar to ordinary ferromagnetic materials, but the spontaneous moment does not correspond to the value expected for full parallel alignment of the (magnetic) dipoles in the substance. Further details on "ferrimagnetic substance" or "ferrimagnetism" can be found in various literatures, e.g., at Page 519–524, Chapter 16, in "Electricity and Magnetism" by B. I Bleaney and B. Bleaney, Oxford, 1975.

As used herein, "a photorecognizable coding pattern" refers to any coding pattern that can be detected and/or assessed by photoanalysis (optical analysis). Any photorecognizable property can be used as the characteristics of the coding pattern. For example, the photorecognizable coding pattern can be the material composition of the microdevice or substrate itself, structural configuration of the microdevice (e.g., a hole in the microdevice or the substrate or a substance immobilized on the microdevice or the substrate), said substance having an optical refractive property that is different from the optical refractive property of the microdevice or the substrate. The versatility of the photorecognizable coding pattern can be based on the shape, number, position distribution, optical refractive property, material composition, or a combination thereof, of the microdevice or the substrate, the hole(s), or other structural configurations, or certain substance(s) located, deposited or immobilized on the microdevice or the substrate. To facilitate optical analysis (or photoanalysis) of encoding patterns, certain microdevices may incorporate "orientation" marks or alignment markers. The orientation markers can be used for indicating which major surface is up and for helping decode the patterns. 1-D and/or 2-D bar coding patterns can also be used as photorecognizable coding pattern in the present microdevices.

As used herein, "a photorecognizable coding pattern on said substrate" means that the photorecognizable coding pattern is located on, in, or within (or inside) the substrate so that the photorecognizable coding pattern is optically detectable. For example, the photorecognizable coding pattern can be located on the surface or on top of the substrate. The photorecognizable coding pattern can also be located within or inside the substrate. In other embodiments, the substrate may have multiple layers and the photorecognizable coding pattern can be located on the surface layer, on top of the surface layer, or can be located within or inside one or more layers.

As used herein, "the photorecognizable coding pattern is fabricated or microfabricated on the substrate" means the use of any microfabrication or micromachining methods to produce or generate encoding patterns on the substrate. Various microfabrication or micromachining protocols such as, pattern masking, photolithography, wet etching, reactive-ion-etching and deep-reactive-ion-etching, etc., can be used.

As used herein, "major axis of the microdevice" refers to the longest dimension of the microdevice. For the microdevices having a thin round-disk shape, the height of the microdevice refers to the thickness of the disk. In this case of thin round-disk shaped microdevices, the major axis refers to any axis in the plane parallel to the major surfaces of the disk. In one preferred embodiment of such round-disk shaped microdevices, the photorecognizable coding patterns are on the plane parallel to the major surfaces of the disk surface, located on the disk surface, or within the disk between the two major surfaces. For the microdevices having a thin rectangular shape, three dimensions are defined, the major axis (i.e., length), the minor axis (i.e., the width) and the height (i.e. the thickness of the rectangular microdevice). In such cases, the major axis of the microdevice is longer than the minor axis and height of the microdevice. The minor axis of the microdevice is longer than or equals to the height of the microdevice. The microdevices may have any other shapes.

As used herein, "said microdevice has a preferential axis of magnetization" means that the induced magnetization of the microdevice under the influence of an applied magnetic field depends on the relative angles of the direction of the applied magnetic field and various axes of the microdevices so that when the microdevices are introduced into a minimum-friction (or little- or no-friction) medium and/or placed on a minimum-friction (or little- or no-friction) surface, the microdevice may rotate or orient itself under the interaction of the applied magnetic field and the induced magnetization to achieve a minimum energy state or stable state. When the microdevices introduced into a minimum friction (or little or no-friction) medium and/or placed on a minimum-friction (or little- or no-friction) surface are in such a minimum energy state, the microdevice's axis that is aligned with the applied magnetic field is the preferential axis of magnetization. The preferential axis of magnetization is determined by the geometry of the microdevice, e.g., the ratio between the dimensions of the major axis and the minor axis, as well as the composition and structural configuration of the microdevices. Depending on the geometry of the microdevice, the preferential axis of magnetization can be a single axis in a particular direction or multiple axes in multiple directions, or even any axis direction lying within a plane. Once the dynamic process of inducing magnetization is over and the microdevice has achieved the minimum energy state in a magnetic field, the induced magnetization along the preferential axis of magnetization (in its absolute magnitude) is larger than or at least equal to induced magnetization along any other axis of the microdevice. In general, for the microdevices of the present invention to rotate or orient itself under the interaction of the applied magnetic field and the induced magnetization, the induced magnetization (in its absolute magnitude) along the preferential axis of magnetization of the microdevice should be at least 20% more than the induced magnetization of the microdevice along at least one other axis. Preferably, the induced magnetization (in its absolute magnitude) along the preferential axis of magnetization of the microdevices of the present invention should be at least 50%, 70%, or 90% more than the induced magnetization of the microdevice along at least one other axis. Even more preferably, the induced magnetization (in its absolute magnitude) along the preferential axis of the magnetization of the microdevices of the present invention should be at least one time, twice, five times, ten times, twenty times, fifty times or even hundred times more than the induced magnetization of the microdevice along at least one other axis. The rotation and orientation of the microdevice under the influence of the applied magnetic field is a dynamic process and may take some time to achieve the minimum energy state or stable state. In an environment where friction or other force, e.g., gravity, exists, the preferential axis of the magnetization of microdevice may not align with the applied magnetic field perfectly even when a steady-state is achieved. Preferably, numerous factors such as the geometry of the microdevice, the direction and strength of the applied magnetic field and other factors (e.g., for a microdevice lying on a support surface, the frictional force that may relate to the property of the support surface may be a factor) can be adjusted to ensure that the preferential axis of magnetization of microdevice is substantially aligned with the applied magnetic field when a steady-state is achieved. For example, for a microdevice having a thin round-disk shape with magnetizable substance inside having a thin disc shape, the preferential axis of magnetization of such microdevice may lie in the plane parallel to the major surfaces of the microdevice (and also parallel to the major surface of the thin disk magnetic substance). When such a microdevice is subject to an applied magnetic field, even if initially the thin disk microdevice lies in the plane normal to the applied magnetic field, the microdevice will re-align itself so that the thin disk plane will be parallel or close-to-parallel to the direction of the magnetic field. In another example, the microdevice has a thin rectangular shape inside which the magnetizable substance forms a magnetic structure such as a magnetic rectangular bar whose length, width and thickness are in the same directions as those of the microdevice itself. The preferential axis of magnetization of such microdevice may be in the same direction as the length-direction of the microdevice and the length direction of the magnetic bar inside the microdevice.

As used herein, "the preferential axis of magnetization of the microdevice is substantially aligned with an applied magnetic field" means that the angle between the preferential axis of the magnetization and the applied magnetic field should be 45 degrees or less. Preferably, the angle between the preferential axis of magnetization and the applied magnetic field should be 15 degrees or less. More preferably, the preferential axis of magnetization is completely aligned with the applied magnetic field. For microdevices whose preferential axis of magnetization is the major axis, then "the preferential axis of magnetization of the microdevice is substantially aligned with an applied magnetic field" means that the angle between the major axis of the microdevice and the applied magnetic field should be 45 degrees or less. For example, for microdevices having thin rectangular shape and having the major axis as the preferential axis of magnetization, an applied magnetic field may result in the formation of a chain of the microdevices along their major axises. When the applied magnetic field rotates for more than 45 degree (e.g. 90 degree), the microdevices would also rotate for the same or similar degrees so that each microdevice in the chain is substantially separated from each other.

As used herein, "the preferential axis of magnetization of the microdevice is substantially aligned with microdevice's major axis" means that the angle between the preferential axis of the magnetization and the major axis should be 45 degrees or less. Preferably, the angle between the preferential axis of magnetization and the major axis should be 15 degrees or less. More preferably, the preferential axis of magnetization is completely aligned with the major axis.

As used herein, "each microdevice in the chain is substantially separated from each other" means that the microdevices are sufficiently separated so that each of the microdevices can be identified and/or analyzed by its respective photorecognizable coding pattern. The degree of the separation among individual microdevices is determined by a number of factors such as the type, number and/or distribution of the photorecognizable coding pattern(s), the geometry of the microdevices, the methods for assessing the photorecognizable coding pattern(s) and the purpose of the identification and/or analysis of the microdevices. Certain touch or overlap among individual microdevices are permissible so long as each of the microdevices can be identified and/or analyzed by its respective photorecognizable coding pattern for the intended purpose. In certain situations, it is preferably that the microdevices are completely separated from each other without any touching or overlap.

As used herein, "said microchannels are sufficiently wide to permit rotation of said microdevices within said microchannels but sufficiently narrow to prevent said microdevices from forming a chain when the major axis of said microdevices is substantially perpendicular to the major axis of said microchannels" means that the width of a microchannel equals to or is larger than the longest dimension of microdevices, e.g., diagonal dimension of a rectangle, within the microchannel to permit rotation of the microdevices within the microchannel. At the same time, the width of a microchannel equals to or is less than 150% of the longest dimension of microdevices, e.g. diagonal dimension of a rectangle, within the microchannel to prevent microdevices from forming a chain (of at least two microdevices) when the major axis of said microdevices is substantially perpendicular to the major axis of said microchannels. Preferably, the width of a microchannel equals to or is less than 150%, 140%, 130%, 120%, 110%, or 105% 102% of the longest dimension of microdevices. "Sufficiently narrow to prevent said microdevices from forming a chain" also means that after the rotation, each microdevice in the chain is substantially separated from each other as defined above. It is not necessary, although permissible, that each of the microchannels within a microchannel array has same width. It is sufficient that each of the microchannels has a width that is compatible to the microdevices to be rotated within the microchannel. Here, the major axis of the microchannel refers to the length direction of the microchannel.

As used herein, "the major axis of said microdevices is substantially perpendicular to the major axis of said microchannels" means that the angle between the major axis of microdevices and the major axis of the microchannel that contains the microdevices equals to or is larger than 45 degrees. Preferably, the angle between the major axis of microdevices and the major axis of the microchannels that contains the microdevices equals to or is larger than 50, 55, 60, 65, 70, 75, 80, 85 and 90 degrees. Here, the major axis of the microchannels refers to the length direction of the microchannels.

As used herein, "the height of the microchannels and/or the constraint on the microdevices by a magnetic field does not allow the microdevices to stand up within the microchannels" means that the height of the microchannels alone, the constraint on the microdevices by a magnetic field alone, or both, may be sufficient to prevent microdevices from taking a position so that the major axis of the microdevices is substantially aligned with the height of the microchannel. In these cases, the dimension of microchannel is defined by its length, width and height. Its length corresponds to the major axis of the microchannel. The microchannel height corresponds to the microchannel axis that is normal to the surface on which the microchannel is positioned. The microchannel width refers to the third dimension. The "major axis of the microdevices is substantially aligned with the height of the microchannel" means that the angle between the major axis of the microdevices and the height of the microchannel equals to is less than 45 degrees. When the constraint on the microdevices by a magnetic field alone is sufficient to prevent microdevices from taking such a prohibitive position, the height of the microchannels becomes irrelevant in this consideration.

As used herein, "said photorecognizable coding pattern corresponds to an entity to be synthesized on said microdevice" means that the entity to be synthesized on a particular microdevice is predetermined according to the photorecognizable coding pattern on that microdevice. The coding pattern can determine the entity to be synthesized on a microdevice in different ways. For example, a coding pattern can have multiple digits and each digit determines a particular synthesis reaction and the collection of all digits collectively determines all synthesis reactions, and hence the identity of the entity to be synthesized. Alternatively, a coding pattern can be an "intact" pattern, i.e., the entire pattern, not a portion or a digit of the pattern, determines the entire synthesis reactions on the microdevice, and hence the identity of the entity to be synthesized.

As used herein, "said microdevices are sorted after each synthesis cycle according to said photorecognizable coding patterns" means that the synthetic steps or orders for making an entity on a particular microdevice are predetermined according to the photorecognizable coding pattern on that microdevice and after each synthesis cycle, the photorecognizable coding pattern on the microdevice is assessed for directing the next synthetic step or order.

As used herein, "electrically conductive or dielectrically polarizable substance" refers to any substance that can be subjected to dielectrophoresis force under appropriate conditions. Depending on the dielectric and electric properties of the substance, the substance may be subject to positive or negative dielctrophpresis forces under certain conditions. Such conditions include, but are not limited to, the frequency of the applied electric field, and the electrical and dielectric property of the medium in which the substance is placed or introduced.

As used herein, "optical labeling substance" refers to any optically detectable substance that can be used to label the microdevices of the present invention to facilitate and/or enable detection and/or identification of the microdevices. Quantum-dot is an example of an optical labeling substance.

As used herein, "scattered-light detectable particle" refers to any particle that can emit unique and identifiable scattered-light upon illumination with light under appropriate conditions. The nano-sized particles with certain "resonance light scattering (RLS)" properties are examples of one type of "scattered-light detectable particle".

As used herein, "quantum dot" refers to a fluorescent label comprising water-soluble semiconductor nanocrystal(s). One unique feature of a quantum dot is that its fluorescent spectrum is related or determined by the diameter of its nanocrystals(s). "Water-soluble" is used herein to mean sufficiently soluble or suspendable in a aqueous-based solution, such as in water or water-based solutions or physiological solutions, including those used in the various fluorescence detection systems as known by those skilled in the art. Generally, quantum dots can be prepared which result in relative monodispersity; e.g., the diameter of the core varying approximately less than 10% between quantum dots in the preparation.

As used herein, "chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips used in the present invention can vary considerably, e.g., from about 1 mm$^2$ to about 0.25 mm$^2$. Preferably, the size of the chips is from about 4 mm$^2$ to about 25 cm$^2$ with a characteristic dimension from about 1 mm to about 7.5 cm. The chip surfaces may be flat, or not flat. The chips with non-flat surfaces may include channels or wells fabricated on the surfaces.

As used herein, "a means for generating a physical force on said chip" refers to any substance, structure or a combination thereof that is capable of generating, in conjunction with an built-in structure on a chip, to generate a desirable physical force on the chip.

As used herein, "physical field," e.g., used itself or used as "physical field in a region of space" or "physical field is generated in a region of space" means that the region of space has following characteristics. When a moiety, alone or bound to a microdevice, of appropriate properties is introduced into the region of space (i.e. into the physical field), forces are produced on the moiety, the microdevice or both, as a result of the interaction between the moiety and/or microdevice and the field. A moiety can be manipulated within a field via the physical forces exerted on the moiety by the field. Exemplary fields include electric, magnetic, acoustic, optical and velocity fields. In the present invention, physical field always exists in a medium in a region of space, and the moiety to be manipulated is suspended in, or is dissolved in, or more generally, is placed in the medium. Typically, the medium is a fluid such as aqueous or non-aqueous liquids, or a gas. Depending on the field configuration, an electric field may produce electrophoretic forces on charged moieties, or may produce conventional dielectrophoretic forces and/or traveling wave dielectrophoretic forces on charged and/or neutral moieties. Magnetic field may produce magnetic forces on magnetic moieties. Acoustic field may produce acoustic radiation forces on moieties. Optical field may produce optical radiation forces on moieties. Velocity field in the medium in a region of space refers to a velocity distribution of the medium that moves in the region of the space. Various mechanisms may be responsible for causing the medium to move and the medium at different positions may exhibit different velocities, thus generating a velocity field. Velocity field may exert mechanical forces on moieties in the medium.

As used herein, "medium (or media)" refers to a fluidic carrier, e.g., liquid or gas, wherein a moiety, alone or bound to a microdevice, is dissolved, suspended or contained.

As used herein, "microfluidic application" refers to the use of microscale devices, e.g., the characteristic dimension of basic structural elements is in the range between less than 1 micron to 1 cm scale, for manipulation and process in a fluid-based setting, typically for performing specific biological, biochemical or chemical reactions and procedures. The specific areas include, but are not limited to, biochips, i.e., chips for biologically related reactions and processes, chem-chips, i.e., chips for chemical reactions, or a combination thereof. The characteristic dimensions of the basic elements refer to the single dimension sizes. For example, for the microscale devices having circular shape structures (e.g. round electrode pads), the characteristic dimension refers to the diameter of the round electrodes. For the devices having thin, rectangular lines as basic structures, the characteristic dimensions may refer to the width or length of these lines.

As used herein, "built-in structures on said substrate of a chip" means that the structures are built into the substrate or the structures are located on the substrate or the structures are structurally linked to the substrate of the chip. In one embodiment, the built-in structures may be fabricated on the substrate. For example, as described in "Dielectrophoretic manipulation of cells using spiral electrodes by Wang et al., *Biophys. J.*, 72:1887–1899 (1997)", spiral electrodes are fabricated on a glass substrate. Here the spiral electrodes are "built-in" structures on the glass substrate. In another embodiment, the "built-in" structures may be first fabricated on one substrate and the structure-containing first substrate may then be attached or bound to a second substrate. Such structures are "built-in" structures not only on the first substrate but also on the second substrate. In still another embodiment, the built-in structures may be attached or bound to the substrate. For example, thin, electrically-conductive wires may be used as electrodes for producing electric field. These electric wires may be bound or attached to a glass substrate. In this case, the electrically-conductive wires are "built-in" structures on the glass substrate. Throughout this application, when it is described that "built-in" structures on the chip or on the substrate are capable of generating physical forces and/or physical fields or these structures generate physical forces and/or physical fields, these structures are used in combination with external signal sources or external energy sources.

As used herein, "micro-scale structures" means that the scale of the internal structures of the apparatus for exerting desired physical forces must be compatible with and useable in microfluidic applications and have characteristic dimension of basic structural elements in the range from about 1 micron to about 20 mm scale.

As used herein, "moiety" refers to any substance whose isolation, manipulation, measurement, quantification, detection or synthesis using the present microdevice is desirable. Normally, the dimension (or the characteristic dimensions) of the moiety should not exceed 1 cm. For example, if the moiety is spherical or approximately spherical, the dimension of the moiety refers to the diameter of the sphere or an approximated sphere for the moiety. If the moiety is cubical or approximately cubical, then the dimension of the moiety refers to the side width of the cube or an approximated cube for the moiety. If the moiety has an irregular shape, the dimension of the moiety may refer to the average between its largest axis and smallest axis. Non-limiting examples of moieties include cells, cellular organelles, viruses, particles, molecules, e.g., proteins, DNAs and RNAs, or an aggregate or complex thereof.

Moiety to be isolated, manipulated, measured, quantified, detected or synthesized includes many types of particles— solid (e.g., glass beads, latex particles, magnetic beads), liquid (e.g., liquid droplets) or gaseous particles (e.g., gas bubble), dissolved particles (e.g., molecules, proteins, antibodies, antigens, lipids, DNAs, RNAs, molecule-complexes), suspended particles (e.g., glass beads, latex particles, polystyrene beads). Particles can be organic (e.g., mammalian cells or other cells, bacteria, virus, or other microorganisms) or inorganic (e.g., metal particles). Particles can be of different shapes (e.g., sphere, elliptical sphere, cubic, discoid, needle-type) and can be of different sizes (e.g., nano-meter-size gold sphere, to micrometer-size cells, to millimeter-size particle-aggregate). Examples of particles include, but are not limited to, biomolecules such as DNA, RNA, chromosomes, protein molecules (e.g., antibodies), cells, colloid particles (e.g., polystyrene beads, magnetic beads), any biomolecules (e.g., enzyme, antigen, hormone etc).

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 micron) with non-compartmentalized circular DNA and ribosomes of about 70 S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, *pseudomonas* and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, "binding partners" refers to any substances that bind to the moieties with desired affinity or specificity. Non-limiting examples of the binding partners include cells, cellular organelles, viruses, particles, microparticles or an aggregate or complex thereof, or an aggregate or complex of molecules, or specific molecules such as antibodies, single stranded DNAs. The binding partner can be a substance that is coated on the surface of the present microdevice. Alternatively, the binding partner can be a substance that is incorporated, e.g., microfabricated, into the material composition of the present microdevice. The material composition of the present microdevice, in addition being a substrate, may possess binding affinity to certain moiety, and thus functioning as a binding partner itself.

As used herein, "an element that facilitates and/or enables manipulation of the microdevice and/or a moiety/microdevice complex" refers to any substance that is itself manipulatable or makes the moiety/microdevice complex manipulatable with the desired physical force(s). Non-limiting examples of the elements include cells, cellular organelles, viruses, particles, microparticles or an aggregate or complex thereof, or an aggregate or complex of molecules. Non-limiting examples of the elements may further include deposited or other-procedure-produced materials with specific physical or chemical properties. Metal films made of Au, Cr, Ti, Pt etc are examples of the elements that can be incorporated into the microdevices and increase electrical conductivity of the microdevices. Insulating materials such as polystyrene, paralene, or other plastic polymers are also examples of the elements that may be incorporated into the microdevices and reduce electrical conductivity of the microdevices.

As used herein, "microparticles" refers to particles of any shape, any composition, any complex structures that are manipulatable by desired physical force(s) in microfluidic settings or applications. One example of microparticles is magnetic beads that are manipulatable by magnetic forces. Another example of a microparticle is a cell that is manipulatable by an electric force such as a traveling-wave dielectrophoretic force. The microparticles used in the methods can have a dimension from about 0.01 micron to about ten centimeters. Preferably, the microparticles used in the methods have a dimension from about 0.01 micron to about several thousand microns. Examples of the microparticles include, but are not limited to, plastic particles, polystyrene microbeads, glass beads, magnetic beads, hollow glass spheres, particles of complex compositions, microfabricated free-standing microstructures, etc. Other particles include cells, cell organelles, large biomolecules such as DNA, RNA and proteins etc.

As used herein, "manipulation" refers to moving or processing of the moieties, and the microdevices disclosed in the present invention, which results in one-, two- or three-dimensional movement of the moiety (and the microdevices). The manipulation can be conducted off a chip or in a chip format, whether within a single chip or between or among multiple chips, or on a substrate or among substrates of an apparatus. "Manipulation" of moieties and the microdevices can also be performed in liquid containers. Non-limiting examples of the manipulations include transportation, focusing, enrichment, concentration, aggregation, trapping, repulsion, levitation, separation, sorting, fractionation, isolation or linear or other directed motion of the moieties. For effective manipulation, the characteristics of the moiety (and the microdevices) to be manipulated and the physical force used for manipulation must be compatible. For example, the microdevices with certain magnetic properties can be used with magnetic force. Similarly, the microdevices with electric charge(s) can be used with electrostatic (i.e. electrophoretic) force. In the case of manipulating microdevices-binding partner-moiety complexes, the characteristics of the moiety, or its binding partner or the microdevices, and the physical force used for manipulation must be compatible. For example, moiety or its binding partner or the microdevices with certain dielectric properties to induce dielectric polarization in the moiety or its binding partner or the microdevices can be used with dielectrophoresis force.

As used herein, "the moiety is not directly manipulatable" by a particular physical force means that no observable movement of the moiety can be detected when the moiety itself not coupled to a binding partner is acted upon by the particular physical force.

As used herein, "physical force" refers to any force that moves the moieties or their binding partners or the corresponding microdevices without chemically or biologically reacting with the moieties and the binding partners, or with minimal chemical or biological reactions with the binding partners and the moieties so that the biological/chemical functions/properties of the binding partners and the moieties are not substantially altered as a result of such reactions. Throughout the application, the term of "forces" or "physical forces" always means the "forces" or "physical forces" exerted on a moiety or moieties, the binding partner(s) and/or the microdevice(s). The "forces" or "physical forces" are always generated through "fields" or "physical fields". The forces exerted on moieties, the binding partner(s) and/or the microdevice(s) by the fields depend on the properties of the moieties, the binding partner(s) and/or the microdevice(s). Thus, for a given field or physical field to exert physical forces on a moiety, it is necessary for the moiety to have certain properties. While certain types of fields may be able to exert forces on different types of moieties having different properties, other types of fields may be able to exert forces on only limited type of moieties. For example, magnetic field can exert forces or magnetic forces only on magnetic particles or moieties having certain magnetic properties, but not on other particles, e.g., polystyrene microdevices. On the other hand, a non-uniform electric field can exert physical forces on many types of moieties such as polystyrene microdevices, cells, and also magnetic particles. It is not necessary for the physical field to be able to exert forces on different types of moieties or different moieties. But it is necessary for the physical field to be able to exert forces on at least one type of moiety or at least one moiety, the binding partner(s) and/or the microdevice(s).

As used here in, "electric forces (or electrical forces)" are the forces exerted on moieties, the binding partner(s) and/or the microdevice(s) by an electric (or electrical) field.

As used herein, "magnetic forces" are the forces exerted on moieties, the binding partner(s) and/or the microdevice(s) by a magnetic field.

As used herein, "acoustic forces (or acoustic radiation forces)" are the forces exerted on moieties, the binding partner(s) and/or the microdevice(s) by an acoustic field.

As used herein, "optical (or optical radiation) forces" are the forces exerted on moieties, the binding partner(s) and/or the microdevice(s) by an optical field.

As used herein, "mechanical forces" are the forces exerted on moieties, the binding partner(s) and/or the microdevice(s) by a velocity field.

As used herein, "sample" refers to anything which may contain a moiety to be isolated, manipulated, measured, quantified or detected by the present microdevices and/or methods. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a mixture of target analyte or enzyme containing molecules prepared *in vitro*.

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

As used herein the term "assessing (or assessed)" is intended to include quantitative and qualitative determination of the identity and/or quantity of a moiety, e.g., a protein or nucleic acid, present in the sample or on the microdevices or in whatever form or state. Assessment would involve obtaining an index, ratio, percentage, visual or other value indicative of the identity of a moiety in the sample and may further involve obtaining a number, an index, or other value indicative of the amount or quantity or the concentration of a moiety present in the sample or on the microdevice or in whatever form or state. Assessment may be direct or indirect.

B. Microdevices and Systems for Forming a Microdevice Array

In one aspect, the present invention is directed to a microdevice, which microdevice comprises: a) a magnetizable substance; and b) a photorecognizable coding pattern, wherein said microdevice has a preferential axis of magnetization.

Any suitable magnetizable substance can be used in the present microdevices. In one example, the magnetizable substance used in the microdevice is a paramagnetic substance, a ferromagnetic substance, a ferrimagnetic substance, or a superparamagnetic substance. In another example, the magnetizable substance used in the microdevice comprises a metal composition. Preferably, the metal composition is a transition metal composition or an alloy thereof such as iron, nickel, copper, cobalt, manganese, tantalum, zirconium and cobalt-tantalum-zirconium (CoTaZr) alloy. In a preferred example, the magnetic substance is a metal oxide $Fe_3O_4$.

The present microdevice can further comprise a non-magnetizable substrate. Any suitable material including silicon, plastic, glass, ceramic, rubber, polymer, silicon dioxide, silicon nitride, aluminum oxide, titanium, aluminum, gold and a combination thereof can be used in the substrate. The magnetizable substance can be linked to the substrate in any form. For example, the magnetizable substance can be made part of the substrate or can be attached or deposited or located on the substrate. In another example, the magnetizable substance can be located within the substrate.

The substrate can be a single layer or can comprise multiple layers such as 3, 4 or more layers. For example, a substrate can have 3 layers. The top and the bottom layers can be made of the same material, e.g., $SiO_2$ (or glass) and the middle layer can contain magnetizable material(s). Alternatively, the top and the bottom layers can have different materials.

The substrate can comprises a surface that is hydrophobic or hydrophilic. The substrate can be in any suitable shape such as rectangle and other regular or irregular shape provided that the microdevice be made to have a preferential axis of magnetization. The substrate can be in any suitable dimension(s). For example, the thickness of the substrate can be from about 0.1 micron to about 500 microns. Preferably, the thickness of the substrate can be from about 1 micron to about 200 microns. More preferably, the thickness of the substrate can be from about 1 micron to about 50 microns. In a specific embodiment, the substrate is a rectangle having a surface area from about 10 squared-microns to about 1,000,000 squared-microns (e.g., 1000 micron by 1000 micron). In another specific embodiment, the substrate is in an irregular shape having a single-dimension from about 1 micron to about 500 microns. In a preferred embodiment, the substrate is a composite comprising silicon, metal film and polymer film. In another preferred embodiment, the substrate can comprise a silicon layer and a metal layer, e.g., an aluminum layer. More preferably, the metal layer can comprise a magnetic material, such as nickel metal or CoTaZr (Cobalt-Tantalum-Zirconium) alloy.

The photorecognizable coding pattern can be based on any suitable photorecognizable (optical) property constructed in or on the microdevice or substrate. For example, the photorecognizable coding pattern can be the material composition of the microdevice itself, a hole in the microdevice, or other structural configurations, or certain substance(s) located, deposited or immobilized on the microdevice or the substrate, or an optical labeling substance or an 1-D and/or a 2-D bar coding pattern. The microdevice or substrate can be patterned. In addition, the surface layer of the substrate or microdevice can be modified. The versatility of the photorecognizable coding pattern can be caused by the shape, number, letters, words, position distribution, optical refractive property, material composition, or a combination thereof, of the substrate, the hole(s) or other structure configurations, or certain substance(s) located, deposited or immobilized on the microdevice or the substrate. In one exemplary microdevice, the microdevice or substrate can have 4 layers. The top and the bottom layers can be made of the same material, e.g., $SiO_2$ (or glass). One of the middle layers can contain paramagnetic material(s), e.g., magnetic alloys. The other middle layer can contain a photorecognizable coding pattern as a encoding layer. Preferably, the paramagnetic layer and the encoding layer do not substantially overlap, or do not overlap at all, to ensure optical detection of the photorecognizable coding pattern in the encoding layer. Alternatively, the top and the bottom layers can have different materials. Exemplary patterns include numbers, letters, structures, 1-D and 2-D barcodes.

Although the microdevice can comprise a single photorecognizable coding pattern, it can also comprise a plurality of photorecognizable coding patterns, e.g., a plurality of holes or other structure configurations, a plurality of numbers, a plurality of letter, and/or a plurality of the substances.

To facilitate optical analysis (or photo-analysis) of encoding patterns, certain microdevices may incorporate "orientation" marks or alignment markers. For example, for the microdevices having thin symmetrical shapes, the microdevices lying flat on either of its major surfaces will look identical, causing difficulties in identification. Therefore, the orientation marks can be used for indicating which major surface is being looked at when the microdevices are lying up and for helping decode the patterns.

The photorecognizable coding pattern can be constructed according to any methods known in the art. For example, the photorecognizable coding pattern can be fabricated or microfabricated on a substrate. Any suitable fabrication or microfabrication method can be used including lithography such as photolithography, electron beam lithography and X-ray lithography (WO 96/39937 and U.S. Pat. Nos. 5,651,900, 5,893,974 and 5,660,680). For example, the fabrication or microfabrication methods can be used directly on a substrate to produce desirable patterns such as numbers, letters, structures, 1-D and 2-D barcodes.

If a substance having an optical refractive property that is different from the optical refractive property of the substrate is used as the photorecognizable coding pattern, the substance can be deposited or immobilized on the substrate by any suitable methods known in the art. For example, the substance used for photorecognizable encoding can be deposited or immobilized on the substrate by evaporation or sputtering methods. The substance can be deposited or immobilized on the substrate directly or via a linker. The linker can be any material or molecules that linking the substance to the substrate. The fabrication or microfabrication methods can be used on the substances deposited on the substrate to produce desirable patterns such as numbers, letters, structures, 1-D and 2-D barcodes. The substance can be immobilized or deposited on the substrate via a covalent or a non-covalent linkage. The substance can be deposited or immobilized on the substrate via specific or non-specific binding.

Any suitable optical labeling substance can be used in the present microdevices. In a specific embodiment, the optical labeling substance used in the present microdevices is a metal film such as Cu, Al, Au, Pt that can be patterned to form photorecognizable encoding patters such as letters, numbers, structures or structural configurations, 1-D or 2-D barcodes. In another specific embodiment, the optical labeling substance used in the present microdevices is a fluorescent substance, a scattered-light detectable particle (See e.g., U.S. Pat. No. 6,214,560) and a quantum dot (See e.g., U.S. Pat. No. 6,252,664).

Any suitable quantum dot can be used in the present microdevices. In a specific embodiment, the quantum dot used in the present microdevices comprises a Cd—X core, X being Se, S or Te. Preferably, the quantum dot can be passivated with an inorganic coating shell, e.g., a coating shell comprising Y-Z, Y being Cd or Zn, and Z being S or Se. Also preferably, the quantum dot can comprise a Cd—X core, X being Se, S or Te, a Y-Z shell, Y being Cd or Zn, and Z being S or Se, and the quantum dot can further be overcoated with a trialkylphosphine oxide.

Any suitable methods can be used to make the CdX core/YZ shell quantum dots water-soluble (See e.g., U.S. Pat. No. 6,252,664). One method to make the CdX core/YZ shell quantum dots water-soluble is to exchange the overcoating layer with a coating which will make the quantum dots water-soluble. For example, a mercaptocarboxylic acid may be used to exchange with the trialkylphosphine oxide coat. Exchange of the coating group is accomplished by treating the water-insoluble quantum dots with a large excess of neat mercaptocarboxylic acid. Alternatively, exchange of the coating group is accomplished by treating the water-insoluble quantum dots with a large excess of mercaptocarboxylic acid in $CHCl_3$ solution (Chan and Nie, 1998, Science 281:2016–2018). The thiol group of the new coating molecule forms Cd (or Zn)—S bonds, creating a coating which is not easily displaced in solution. Another method to make the CdX core/YZ shell quantum dots water-soluble is by the formation of a coating of silica around the dots (Bruchez, Jr. et al., 1998, Science 281: 2013–2015). An extensively polymerized polysilane shell imparts water solubility to nanocrystalline materials, as well as allowing further chemical modifications of the silica surface. Generally, these "water-soluble" quantum dots require further functionalization to make them sufficiently stable in an aqueous solution for practical use in a fluorescence detection system (See e.g., U.S. Pat. No. 6,114,038), particularly when exposed to air (oxygen) and/or light. Water-soluble functionalized nanocrystals are extremely sensitive in terms of detection, because of their fluorescent properties (e.g., including, but not limited to, high quantum efficiency, resistance to photobleaching, and stability in complex aqueous environments); and comprise a class of semiconductor nanocrystals that may be excited with a single peak wavelength of light resulting in detectable fluorescence emissions of high quantum yield and with discrete fluorescence peaks (e.g., having a narrow spectral band ranging between about 10 nm to about 60 nm).

The quantum dot used in the present microdevice can have any suitable size. For example, the quantum dot can have a size ranging from about 1 nm to about 100 nm.

The microdevice of the present invention can comprise a single quantum dot. Alternatively, the microdevice of the present invention can comprise a plurality of quantum dots. Preferably, the microdevice of the present invention comprises at least two quantum dots that have different sizes.

The microdevice of the present invention can comprise a single optical labeling substance. Alternatively, the microdevice of the present invention can comprise a plurality of optical labeling substances. For example, the microdevice of the present invention can comprise at least two different types of optical labeling substances.

In a specific embodiment, the microdevice of the present invention comprises an electrically conductive or dielectrically polarizable substance. Such electrically conductive or dielectrically polarizable substance incorporated into the microdevice may alter the overall electrical and/or dielectric properties of the microdevice, resulting in a change in the interaction between the microdevice and an applied electrical field and a change in the electrical field-induced force (e.g., dielectrophoretic force, traveling wave dielectrophoretic forces) acting on the microdevice.

In choosing the type, materials, compositions, structures and sizes of the microdevices, these properties or parameters of the microdevices should be compatible with the isolation, manipulation, detection or synthesis format in the specific applications. For example, the microdevices may be used to isolate target analyte-molecules (e.g. proteins) from a molecule mixture. If the isolation uses dielectrophoretic forces, then the microdevices should have the desired dielectric properties. If the isolation/manipulation utilizes magnetic forces, then the microdevices should have incorporated magnetic materials such as ferro- or ferri-magnetic materials.

The microdevice can also comprise a binding partner that is capable of binding to a moiety, e.g., a moiety to be isolated, manipulated, detected or synthesized. Preferably, the binding partner specifically binds to the moiety. Throughout this application, whenever the binding partners are described or used, they are always coupled onto the microdevices of the present inventions. For example, when the complexes between the binding partners and the moieties are discussed, the complexes between the moieties and the binding partners that are coupled on the microdevices are referred to.

Any suitable binding partner including the binding partners disclosed in the co-pending U.S. patent application Ser. Nos. 09/636,104, filed Aug. 10, 2000 and 09/679, 024, filed Oct. 4, 2000, the disclosures of which are incorporated by reference in its entirety, can be used. For example, the binding partners can be cells such as animal, plant, fungus or bacterium cells; cellular organelles such as nucleus, mitochondria, chloroplasts, ribosomes, ERs, Golgi apparatuses, lysosomes, proteasomes, secretory vesicles, vacuoles or microsomes; viruses, microparticles or an aggregate or complex thereof. Other binding partners may be molecules that have been immobilized on the microdevices' surfaces. For example, antibodies can be immobilized or bound on to the microdevices' surfaces. The antibody-bound microdevices can then be used to capture and bind to target proteins in a molecule mixture or to capture and bind to target cells in a cell mixture. Oligo-dT (e.g. 25 mer of T) can be immobilized onto the microdevices' surfaces. The oligo-dT bound microdevices can then be used to capture >mRNA from a molecule mixture. Other molecules may be used as binding partners for capturing or binding DNA molecules. Nucleic acid fragments, e.g., DNA, RNA, PNA segments of specific sequences, may be used to hybridize to target nucleic acid, DNA, RNA or PNA, molecule. Other binding partners may be molecules or functional groups that are attached or otherwise bound to the microdevices' surfaces, resulting in functionalized surfaces to which various chemical/biochemical/biological reactions can occur. In some embodiments, these various reactions may allow the moieties to bind to the microdevices so that the moieties can be manipulated, isolated, or detected via the use of the microdevices of the present invention. In some other exemplary embodiments, the functionalized surfaces allow synthesis reaction to take place on the microdevices' surfaces. Examples of such synthesis include the synthesis of nucleic acids, (e.g. DNA, RNA), or the synthesis of peptides or proteins, etc. Examples of such functionalized surfaces include, but are not limited to, surfaces derivatized with carboxyl, amino, hydroxyl, sulfhydryl, epoxy, ester, alkene, alkyne, alkyl, aromatic, aldehyde, ketone, sulfate, amide, urethane group(s), or their derivatives thereof.

The choice of the microdevices is further related to the specific isolation, manipulation detection or synthesis uses. For example, for separating target moiety from a mixture of molecules and particles by dielectrophoresis manipulation, binding partner's or microdevice's dielectric properties should be significantly different from those of molecules and particles so that when binding partners are coupled with the target moiety, the moiety-binding-partner-microdevices complexes may be selectively manipulated by dielectrophoresis. In an example of separating target cancer cells from a mixture of normal cells, the cancer cells may have similar dielectric properties to those of normal cells and all the cells behave similarly in their dielectrophoretic responses, e.g., negative dielectrophoresis. In this case, the binding partners or the microdevice preferably should be more dielectrically-polarizable than their suspending medium and will exhibit positive dielectrophoresis. Thus, such microdevices-binding partners-cancer-cell complexes can be selectively manipulated through positive dielectrophoresis forces while other cells experience negative dielectrophoresis forces.

The microdevice can comprise a single binding partner. Alternatively, it can be used in a high throughput analysis and can comprise a plurality of binding partners capable of binding or specifically binding to different moieties to be isolated, manipulated or detected, or synthesized.

Since the present microdevice contains magnetizable substance, the microdevice, microdevice-moiety complex, or microdevice-binding partner-moiety complex can always be rotated or otherwise moved or manipulated with magnetic forces. Magnetic forces refer to the forces acting on a particle due to the application of a magnetic field. In general, particles have to be magnetic (e.g. paramagnetic, ferromagnetic) or magnetizable when sufficient magnetic forces are needed to manipulate particles. We consider a typical magnetic particle made of super-paramagnetic material. When the magnetic particle is subjected to a magnetic field $\overline{B}$, a magnetic dipole $\overline{\mu}$ is induced in the magnetic particle $$\overline{\mu} = V_p(\chi_p - \chi_m)\frac{\overline{B}}{\mu_m},$$
$$= V_p(\chi_p - \chi_m)\overline{H}_m$$

where $V_p$ is the magnetic-particle volume, $\chi_p$ and $\chi_m$ are the volume susceptibility of the magentic particle and its surrounding medium, $\mu_m$ is the magnetic permeability of medium, $\overline{H}_m$ is the magnetic field strength. The magnetic force $\overline{F}_{magnetic}$ acting on the magentic particle is determined by the magnetic dipole moment and the magnetic field gradient:

$$\overline{F}_{magnetic} = -0.5 V_p(\chi_p - \chi_m)\overline{H}_m \cdot \nabla \overline{B}_m,$$

where the symbols "•" and "∇" refer to dot-product and gradient operations, respectively. Clearly, whether there is magnetic force acting on a particle depends on the difference in the volume susceptibility between the magnetic particle and its surrounding medium. Typically, magnetic particles are suspended in a liquid, non-magnetic medium (the volume susceptibility is close to zero) thus it is necessary to utilize magnetic particles (its volume susceptibility is much larger than zero). The velocity $v_{particle}$ of the magnetic particle under the balance between magnetic force and viscous drag is given by:

$$v_{particle} = \frac{\overline{F}_{magnetic}}{6\pi r \eta_m}$$

where r is the particle radius and $\eta_m$ is the viscosity of the surrounding medium. Thus to achieve sufficiently large magnetic manipulation force, the following factors should be considered: (1) the volume susceptibility of the magnetic particles should be maximized; (2) magnetic field strength should be maximized; and (3) magnetic field strength gradient should be maximized.

Paramagnetic substances are preferred whose magnetic dipoles are induced by externally applied magnetic fields and return to zero when external field is turned off. Examples of the paramagnetic substances include the commercially available paramagnetic or other magnetic particles. Many of these particles range from submicron (e.g., 50 nm–0.5 micron) up to tens of microns. They may have different structures and compositions. One type of magnetic particle has ferromagnetic materials encapsulated in thin polymer layer, e.g., polystyrene. Another type of magnetic particle has ferromagnetic nanoparticles filled into the poles of porous beads e.g., polystyrene beads. The surface of both types of these particles can be polystyrene in nature and may be modified to link to various types of molecules. In still another type of magnetic particle, ferro-magnetic materials can be incorporated uniformly into the particles during the polymerization process. Thus, in certain embodiments of the microdevices of the present invention, these paramagnetic or magnetic particles may be incorporated into the microdevices so that the microdevices comprise the magnetizable substances.

Exemplary embodiments of the magnetizable substance comprised in the microdevices may include paramagnetic substance, ferromagnetic substance, ferrimagnetic substance, or superparamagnetic substance that are directly deposited or fabricated or incorporated into the microdevices. In one example, the metal composition such as transition metal composition (e.g., iron, nickel, copper, cobalt, manganese, tantalum, zirconium) or an alloy (e.g., cobalt-tantalum-zirconium (CoTaZr) alloy, iron-nickel alloy) composition may be deposited into the microdevices. Various methods such as electroplating (e.g., for making iron-nickel alloy), sputtering (e.g. for making CoTaZr alloy), can be used for depositing magnetizable substances. A number of methods for depositing and/or producing magnetizable substances (e.g. magnetic, paramagnetic, ferro magnetic substances) are described in the U.S. patent application Ser. No. 09/685,410, filed on Oct. 10, 2000, titled "Individually Addressable Micro-Electromagnetic Unit Array Chips in Horizontal Configurations" and naming Wu et al as inventors. This patent application Ser. No. 09/685, 410 is incorporated by reference in its entirety.

The rotation or manipulation of the microdevices, microdevice-moiety complex, or microdevice-binding partner-moiety complex, requires the generation of magnetic field distribution over microscopic scales. One desirable feature of a microdevice is that it has large magnetic susceptibility. Another desirable feature is that it has small residue magnetic polarization after the applied magnetic field/force is turned off. One approach for generating such magnetic fields is the use of microelectromagnetic units. Such units can induce or produce magnetic fields when an electrical current is applied. The on/off status and the magnitude of the electrical current applied to each unit will determine the magnetic field distribution. The structure and dimension of the microelectromagnetic units may be designed according to the requirement of the magnetic field distribution. Manipulation of the microdevices, microdevice-moiety complex, or microdevice-binding partner-moiety complex includes the directed movement, focusing and trapping of them. The motion of magnetic particles in a magnetic field is termed "magnetophoresis". Theories and practice of magnetophoresis for cell separation and other applications may be found in various literatures (e.g., Magnetic Microspheres in Cell Separation, by Kronick, P. L. in Methods of Cell Separation, Volume 3, edited by N. Catsimpoolas, 1980, pages 115–139; Use of magnetic techniques for the isolation of cells, by Safarik I. And Safarikova M., in J. of Chromatography, 1999, Volume 722(B), pages 33–53; A fully integrated micromachined magnetic particle separator, by Ahn C. H. et al., in J. of Microelectromechanical systems, 1996, Volume 5, pages 151–157).

The microdevice can further comprise an element that facilitates and/or enables manipulation of the microdevice and/or a moiety/microdevice complex or synthesis on the microdevice. Any suitable element that can be incorporated to the microdevice and that can alter certain properties of the microdevice can be used. For example, the element can be electrically-conductive or dielectrically-polarizable or electrically-insulating materials to facilitate and/or enable manipulation by dielectrophoresis force, materials having high or low acoustic impedance to facilitate and/or enable manipulation by acoustic force, or charged materials to facilitate and/or enable manipulation by electrostatic force, etc. The element can be a material of certain composition, a cell, a cellular organelle, a virus, a microparticle, an aggregate or complex of molecules and an aggregate or complex thereof. In addition, the binding partners disclosed above and disclosed in the co-pending U.S. patent application Ser. No. 09/636,104, filed Aug. 10, 2000 can also be used as the element(s) that facilitates and/or enables manipulation of the microdevice and/or a moiety/microdevice complex or synthesis on the microdevice. Non-limiting examples of the elements may further include deposited or other-procedure-produced materials with specific physical or chemical properties. Metal films made of Au, Cr, Ti, Pt etc are examples of the elements that can be incorporated into the microdevices and increase electrical conductivity of the microdevices. Insulating materials such as polystyrene, paralene, or other plastic polymers are also examples of the elements that may be incorporated into the microdevices and reduce electrical conductivity of the microdevices.

The element can facilitate and/or enable manipulation of the microdevice and/or a moiety/microdevice complex by any suitable physical force including the physical forces disclosed in the co-pending U.S. patent application Ser. No. 09/636,104, filed Aug. 10, 2000. For instance, a dielectrophoresis force, a traveling-wave dielectrophoresis force, an acoustic force such as one effected via a standing-wave acoustic field or a traveling-wave acoustic field, an electrostatic force such as one effected via a DC electric field, a mechanical force such as fluidic flow force, or an optical radiation force such as one effected via an optical intensity field generated by laser tweezers, can be used.

Dielectrophoresis refers to the movement of polarized particles, e.g., microdevices, microdevice-moiety complex, or microdevice-binding partner-moiety complex, in a non-uniform AC electrical field. When a particle is placed in an electrical field, if the dielectric properties of the particle and its surrounding medium are different, dielectric polarization will occur to the particle. Thus, the electrical charges are induced at the particle/medium interface. If the applied field is non-uniform, then the interaction between the non-uniform field and the induced polarization charges will produce a net force acting on the particle to cause particle motion towards the region of strong or weak field intensity. The net force acting on the particle is called dielectrophoretic force and the particle motion is dielectrophoresis. Dielectrophoretic force depends on the dielectric properties of the particles, particle surrounding medium, the frequency of the applied electrical field and the field distribution.

Traveling-wave dielectrophoresis is similar to dielectrophoresis in which the traveling-electric field interacts with the field-induced polarization and generates electrical forces acting on the particles. Particles, e.g., microdevices, microdevice-moiety complex, or microdevice-binding partner-moiety complex, are caused to move either with or against the direction of the traveling field. Traveling-wave dielectrophoretic forces depend on the dielectric properties of the particles and their suspending medium, the frequency and the magnitude of the traveling-field. The theory for dielectrophoresis and traveling-wave dielectrophoresis and the use of dielectrophoresis for manipulation and processing of microparticles may be found in various literatures (e.g., "Non-uniform Spatial Distributions of Both the Magnitude and Phase of AC Electric Fields determine Dielectrophoretic Forces by Wang et al., in *Biochim Biophys Acta* Vol. 1243, 1995, pages 185–194", "Dielectrophoretic Manipulation of Particles by Wang et al, in IEEE Transaction on Industry Applications, Vol. 33, No. 3, May/June, 1997, pages 660–669", "Electrokinetic behavior of colloidal particles in traveling electric fields: studies using yeast cells by Huang et al, in J. Phys. D: Appl. Phys., Vol. 26, pages 1528–1535", "Positioning and manipulation of cells and microparticles using miniaturized electric field traps and traveling waves. By Fuhr et al., in Sensors and Materials. Vol. 7: pages 131–146", "Dielectrophoretic manipulation of cells using spiral electrodes by Wang, X-B. et al., in *Biophys. J*. Volume 72, pages 1887–1899, 1997", "Separation of human breast cancer cells from blood by differential dielectric affinity by Becker et al, in Proc. Natl. Acad. Sci., Vol. , 92, January 1995, pages 860–864"). The manipulation of microparticles with dielectrophoresis and traveling wave dielectrophoresis includes concentration/aggregation, trapping, repulsion, linear or other directed motion, levitation, and separation of particles. Particles may be focused, enriched and trapped in specific regions of the electrode reaction chamber. Particles may be separated into different subpopulations over a microscopic scale. Particles may be transported over certain distances. The electrical field distribution necessary for specific particle manipulation depends on the dimension and geometry of microelectrode structures and may be designed using dielectrophoresis theory and electrical field simulation methods.

The dielectrophoretic force $F_{DEP_z}$ acting on a particle of radius r subjected to a non-uniform electrical field may be given, under dipole approximation, by $$F_{DEP_z} = 2\pi \in_m r^3 \chi_{DEP} \nabla E^2_{rms} \cdot \vec{a}_z$$

where $E_{rms}$ is the RMS value of the field strength, $\in_m$ is the dielectric permitivity of the medium. $\chi_{DEP}$ is the particle dielectric polarization factor or dielectrophoresis polarization factor, given, under dipole approximation, by $$\chi_{DEP} = \text{Re}\left(\frac{\varepsilon_p^* - \varepsilon_m^*}{\varepsilon_p^* + 2\varepsilon_m^*}\right),$$

"Re" refers to the real part of the "complex number". The symbol $$\varepsilon_x^* = \varepsilon_x - j\frac{\sigma_x}{2\pi f}$$

is the complex permitivity (of the particle x=p, and the medium x=m). The parameters $\in_p$ and $\sigma_p$ are the effective permitivity and conductivity of the particle, respectively. These parameters may be frequency dependent. For example, a typical biological cell will have frequency dependent, effective conductivity and permitivity, at least, because of cytoplasm membrane polarization.

The above equation for the dielectrophoretic force can also be written as $$F_{DEP_z} = 2\pi \in_m r^3 \chi_{DEP} V^2 p(z) \vec{a}_z$$

where p(z) is the square-field distribution for a unit-voltage excitation (V=1 V) on the electrodes, V is the applied voltage.

There are generally two types of dielectrophoresis, positive dielectrophoresis and negative dielectrophoresis. In positive dielectrophoresis, particles are moved by dielectrophoresis forces towards the strong field regions. In negative dielectrophoresis, particles are moved by dielectrophoresis forces towards weak field regions. Whether particles exhibit positive and negative dielectrophoresis depends on whether the particles are more or less polarizable than the surrounding medium.

Traveling-wave DEP force refers to the force that is generated on particles or molecules due to a traveling-wave electric field. A traveling-wave electric field is characterized by the non-uniform distribution of the phase values of AC electric field components.

Here we analyze the traveling-wave DEP force for an ideal traveling-wave field. The dielectrophoretic force $F_{DEP}$ acting on a particle of radius r subjected to a traveling-wave electrical field $E_{TWD} = E \cos(2\pi(ft-z/\lambda_0)\vec{a}_x$ (i.e., a x-direction field is traveling along the z-direction) is given, under dipole approximation, by $$F_{TWD} = -2\pi \in_m r^3 \zeta_{TWD} E^2 \cdot \vec{a}_z$$

where E is the magnitude of the field strength, $\in_m$ is the dielectric permitivity of the medium. $\zeta_{TWD}$ is the particle polarization factor, given, under dipole approximation, by $$\zeta_{TWD} = \text{Im}\left(\frac{\varepsilon_p^* - \varepsilon_m^*}{\varepsilon_p^* + 2\varepsilon_m^*}\right),$$

"Im" refers to the imaginary part of the "complex number". The symbol $$\varepsilon_x^* = \varepsilon_x - j\frac{\sigma_x}{2\pi f}$$

is the complex permitivity (of the particle x=p, and the medium x=m). The parameters $\in_p$ and $\sigma_p$ are the effective permitivity and conductivity of the particle, respectively. These parameters may be frequency dependent.

Particles such as biological cells having different dielectric properties (as defined by permitivity and conductivity) will experience different dielectrophoretic forces. For traveling-wave DEP manipulation of particles (including biological cells), traveling-wave DEP forces acting on a particle of 10 micron in diameter can vary between 0.01 and 10000 pN.

A traveling wave electric field can be established by applying appropriate AC signals to the microelectrodes appropriately arranged on a chip. For generating a traveling-wave-electric field, it is necessary to apply at least three types of electrical signals each having a different phase value. One method to produce a traveling wave electric field is to use four phase-quardrature signals (0, 90, 180 and 270 degrees) to energize four linear, parallel electrodes patterned on the chip surface. This set of four electrodes forms a basic, repeating unit. Depending on the applications, there may be more than two such units that are located next to each other. This will produce a traveling-electric field in the space above or near the electrodes. As long as electrode elements are arranged following certain spatially sequential orders, applying phase-sequenced signals will result in establishment of traveling electrical fields in the region close to the electrodes.

Both dielectrophoresis and traveling-wave dielectrophoresis forces acting on particles, e.g., microdevices, microdevice-moiety complex, or microdevice-binding partner-moiety complex, depend on not only the field distributions (e.g., the magnitude, frequency and phase distribution of electrical field components; the modulation of the field for magnitude and/or frequency) but also the dielectric properties of the particles and the medium in which particles are suspended or placed. For dielectrophoresis, if particles are more polarizable than the medium (e.g., having larger conductivities and/or permitivities depending on the applied frequency), particles will experience positive dielectrophoresis forces and be directed towards the strong field regions. The particles that are less polarizable than the surrounding medium will experience negative dielectrophoresis forces and be directed towards the weak field regions. For traveling wave dielectrophoresis, particles may experience dielectrophoresis forces that drive them in the same direction as the field is traveling direction or against it, dependent on the polarization factor $\zeta_{TWD}$. The following papers provide basic theories and practices for dielectrophoresis and traveling-wave-dielectrophoresis: Huang, et al., *J. Phys. D: Appl. Phys.* 26:1528–1535 (1993); Wang, et al., *Biochim. Biophys. Acta.* 1243:185–194 (1995); Wang, et al., *IEEE Trans. Ind. Appl.* 33:660–669 (1997).

Microdevices, microdevice-moiety complex, or microdevice-binding partner-moiety complex, may be manipulated using acoustic forces, i.e., using acoustic fields. In one case, a standing-wave acoustic field is generated by the superimposition of an acoustic wave generated from an acoustic wave source and its reflective wave. Particles in standing-wave acoustic fields experience the so-called acoustic radiation force that depends on the acoustic impedance of the particles and their surrounding medium. Acoustic impedance is the product of the density of the material and the velocity of acoustic-wave in the material. Particles with higher acoustic impedance than the surrounding medium are directed towards the pressure nodes of the standing wave acoustic field. Particles experience different acoustic forces in different acoustic field distributions.

One method to generate an acoustic wave source is to use piezoelectric material. These materials, upon applying electrical fields at appropriate frequencies, can generate mechanical vibrations that are transmitted into the medium surrounding the materials. One type of piezoelectric material is piezoelectric ceramics. Microelectrodes may be deposited on such ceramics to activate the piezoelectric ceramic and thus to produce appropriate acoustic wave fields. Various geometry and dimensions of microelectrodes may be used according to the requirements of different applications. Reflective walls are needed to generate a standing-wave acoustic field. Acoustic wave fields of various frequencies may be applied, i.e., fields at frequencies between kHz and hundred megahertz. In another case, one could use a non-standing wave acoustic field, e.g., a traveling-wave acoustic field. A traveling-wave acoustic field may exert forces on particles (see e.g., see, "Acoustic radiation pressure on a compressible sphere, by K. Yoshioka and Y. Kawashima in Acustica, 1955, Vol. 5, pages 167–173"). Particles not only experience forces from acoustic fields directly but also experience forces due to surrounding fluid because the fluid may be induced to move by the traveling-wave acoustic field. Using acoustic fields, particles may be focussed, concentrated, trapped, levitated and transported in a microfluidic environment. Another mechanism for producing forces on particles in an acoustic field is through acoustic-induced fluid convection. An acoustic field produced in a liquid may induce liquid convection. Such convection is dependent on the acoustic field distribution, properties of the liquid, and the volume and structure of the chamber in which the liquid is placed. Such liquid convection will impose forces on particles placed in the liquid and those forces may be used for manipulating particles. One example where such manipulating forces may be exploited is for enhancing the mixing of liquids or the mixing of particles in a liquid. For the present invention, such convection may be used to enhance the mixing of the binding partners coupled onto the microdevices with moiety in a suspension and to promote the interaction between the moiety and the binding partners.

A standing plane wave of ultrasound can be established by applying AC signals to the piezoelectric transducers. For example, the standing wave spatially varying along the z axis in a fluid can be expressed as:

$$\Delta p(z) = p_0 \sin(kz)\cos(\omega t)$$

where $\Delta p$ is acoustic pressure at z, $p_0$ is the acoustic pressure amplitude, k is the wave number ($2\pi/\lambda$, where $\lambda$ is the wavelength), z is the distance from the pressure node, $\omega$ is the angular frequency, and t is the time. According to the theory developed by Yoshioka and Kawashima (see, "Acoustic radiation pressure on a compressible sphere, by K. Yoshioka and Y. Kawashima in Acustica, 1955, Vol. 5, pages 167–173"), the radiation force $F_{acoustic}$ acting on a spherical particle in the stationary standing wave field is given by (see "Studies on particle separation by acoustic radiation force and electrostatic force by Yasuda K. et al. in Jpn. J. Appl. Physics, 1996, Volume 35, pages 3295–3299")

$$F_{acoustic} = -\frac{4\pi}{3} r^3 k \, E_{acoustic} A \sin(2kz)$$

where r is the particle radius, $E_{acoustic}$ is the average acoustic energy density, A is a constant given by $$A = \frac{5\rho_p - 2\rho_m}{2\rho_p + \rho_m} - \frac{\gamma_p}{\gamma_m}$$

where $\rho_m$ and $\rho_p$ are the density of the particle and the medium, $\gamma_m$ and $\gamma_p$ are the compressibility of the particle and medium, respectively. A is termed herein as the acoustic-polarization-factor.

When A>0, the particle moves towards the pressure node (z=0) of the standing wave.

When A<0, the particle moves away from the pressure node.

Clearly, particles of different density and compressibility will experience different acoustic-radiation-forces when placed into the same standing acoustic wave field. For example, the acoustic radiation force acting on a particle of 10 micron diameter can vary between 0.01 and 1000 pN, depending on the established acoustic energy density distribution.

Piezoelectric transducers are made from "piezoelectric materials" that produce an electric field when exposed to a change in dimension caused by an imposed mechanical force (piezoelectric or generator effect). Conversely, an applied electric field will produce a mechanical stress (electrostrictive or motor effect) in the materials. They transform energy from mechanical to electrical and vice-versa. The piezoelectric effect was discovered by Pierre Curie and his brother Jacques in 1880. It is explained by the displacement of ions, causing the electric polarization of the materials' structural units. When an electric field is applied, the ions are displaced by electrostatic forces, resulting in the mechanical deformation of the whole material.

Microdevices, microdevice-moiety complex, or microdevice-binding partner-moiety complex, may be manipulated using DC electric fields. A DC electric field can exert an electrostatic force on charged particles. The force depends on the charge magnitude and polarity of the particles as well as on the magnitude and direction of the field. The particles with positive and negative charges may be directed to electrodes with negative and positive potentials, respectively. By designing a microelectrode array in a microfluidic device, electric field distributions may be appropriately structured and realized. With DC electric fields, microparticles may be concentrated (enriched), focussed and moved (transported) in a microfluidic device. Proper dielectric coating may be applied on to DC electrodes to prevent and reduce undesired surface electrochemistry and to protect electrode surfaces.

The electrostatic force $F_E$ on a particle in an applied electrical field $E_z \vec{a}_z$ can be given by $$F_E = Q_p E_z \vec{a}_z$$

where $Q_p$ is the effective electric charge on the particle. The direction of the electrostatic force on a charged particle depends on the polarity of the particle charge as well as the direction of the applied field.

Thermal convection forces refer to the forces acting on particles, e.g., microdevices, microdevice-moiety complex, or microdevice-binding partner-moiety complex, due to the fluid-convection (liquid-convection) that is induced by a thermal gradient in the fluid. Thermal diffusion in the fluid drives the fluid towards thermal equilibrium. This causes a fluid convection. In addition, the density of aqueous solutions tends to decrease with increasing temperature. Such density differences are also not stable within a fluid resulting in convection. Thermal convection may be used to facilitate liquid mixing. Directed thermal convection may act as an active force.

Thermal gradient distributions may be established within a chip-based chamber where heating and/or cooling elements may be incorporated into the chip structure. A heating element may be a simple joule-heating resistor coil. Such a coil could be microfabricated onto the chip. As an example, consider a coil having a resistance of 10 ohm. Applying 0.2 A through the coil would result in 0.4 W joule heating-power. When the coil is located in an area<100 micron², this is an effective way of heat generation. Similarly, a cooling element may be a Peltier element that could draw heat upon applying electric potentials.

As an exemplary embodiment, the microdevices of the present invention may be used on a chip that incorporates an array of individually addressable heating elements. These heating elements may be positioned or structurally arranged in certain order so that when each, some, or all of the elements are activated, thermal gradient distributions will be established to produce thermal convection. For example, if one heating element is activated, temperature increases in the liquid in the neighborhood of that element will induce fluid convection. In another exemplary embodiment, the chip may comprise multiple, interconnected heating units so that these units can be turned on or off in a synchronized order. Yet, in another example, the chip may comprise only one heating element that can be energized to produce heat and induce thermal convection in the liquid fluid.

Other physical forces may be applied. For example, mechanical forces, e.g., fluidic flow forces, may be used to transport microparticles, e.g., microdevices, microdevice-moiety complex, or microdevice-binding partner-moiety complex. Optical radiation forces as exploited in "laser tweezers" may be used to focus, trap, levitate and manipulate microparticles. The optical radiation forces are the so-called gradient-forces when a material (e.g., a microparticle) with a refractive index different from that of the surrounding medium is placed in a light gradient. As light passes through a polarizable material, it induces fluctuating dipoles. These dipoles interact with the electromagnetic field gradient, resulting in a force directed towards the brighter region of the light if the material has a refractive index larger than that of the surrounding medium. Conversely, an object with a refractive index lower than the surrounding medium experiences a force drawing it towards the darker region. The theory and practice of "laser tweezers" for various biological application are described in various literatures (e.g., "Making light work with optical tweezers, by Block S. M., in Nature, 1992, Volume 360, pages 493–496"; "Forces of a single-beam gradient laser trap on a dielectric sphere in the ray optics regime, by Ashkin, A., in Biophys. J., 1992, Volume 61, pages 569–582"; "Laser trapping in cell biology, by Wright et al., in IEEE J. of Quantum Electronics, 1990, Volume 26, pages 2148–2157"; "Laser manipulation of atoms and particles, by Chu S. in Science, 1991, Volume 253, pages 861–866"). The light field distribution and/or light intensity distribution may be produced with built-in optical elements and arrays on a chip and external optical signal sources, or may be produced with built-in electro-optical elements and arrays on a chip and the external structures are electrical signal sources. In the former case, when the light produced by the optical signal sources passes through the built-in optical elements and arrays, light is processed by these elements/arrays through, e.g. reflection, focusing, interference, etc. Optical field distributions are generated in the regions around the chip. In the latter case, when the electrical signals from the external electrical signal sources are applied to the built-in electro-optical elements and arrays, light is produced from these elements and arrays and optical fields are generated in the regions around the chip.

Although the microdevices can comprise a single element that can facilitate and/or enable manipulation of the microdevice by one type of physical forces or synthesis on the microdevice, they may also be used in high throughput analysis and preferably comprise a plurality of elements, each of the elements facilitates and/or enables manipulation of the microdevice and/or the moiety/microdevice complex by a different physical force. For example, the element can be a conductive or insulating material for manipulation by a dielectrophoresis force, a material having high or low acoustic impedance for manipulation by acoustic force, and/or a charged material for manipulation by a electrostatic force, etc.

In a preferred embodiment, the microdevice comprises a binding partner that is capable of binding or specifically binding to a moiety to be isolated, manipulated, detected or synthesized and an element that facilitates and/or enables manipulation of the microdevice and/or the moiety/microdevice complex. More preferably, the microdevice(s) comprises a plurality of binding partners, each of the binding partners is capable of binding or specifically binding to a different moiety to be isolated, manipulated, detected or synthesized and a plurality of the elements, each of the elements facilitates and/or enables manipulation of the microdevice and/or the moiety/microdevice complex by a different physical force.

The microdevice can further comprise a detectable marker or a molecular tag. Exemplary detectable markers include dyes, radioactive substances and fluorescent substances. Exemplary detectable molecular tags include nucleic acid, oligonucleotide, protein and peptide sequences.

In a specific embodiment, the present microdevice has a thin rectangular shape and has a major axis (length) to minor axis (width) ratio of at least about 1.2, and preferably at least about 1.5, and has a thickness (height) smaller than both major axis and minor axis. In another specific embodiment, the present microdevice comprises at least two rectangular-shaped strips (or bars) or near-rectangular-shaped strips (or bars) of the paramagnetic substance. Preferably, at least two strips (or bars) of the paramagnetic substance are separated and located on each side of the microdevice along the major axis of the microdevice. More preferably, a metal film is processed to have a photorecognizable pattern that is located between the at least two strips (or bars) of the paramagnetic substances. More preferably, the metal film comprises aluminum. Also more preferably, the present microdevice has unequal number of the paramagnetic substance strip(s) (or bars) on each side along the major axis of the microdevice. In still another specific embodiment, the present microdevice comprises two strips (or bars) of the paramagnetic substance along the major axis of the microdevice. Preferably, the two strips (or bars) of the paramagnetic substance have fingers on both ends. In yet another specific embodiment, the paramagnetic substance in the present microdevice forms a strip (or bar) along the major axis of the microdevice and said strip (or bar) has fingers on both ends.

In another aspect, the present invention is directed to a system for forming a microdevice array, which system comprises: a) a plurality of microdevices, each of the microdevices comprising a magnetizable substance and a photorecognizable coding pattern, wherein said microdevices have a preferential axis of magnetization; and b) a microchannel array comprising a plurality of microchannels, said microchannels are sufficiently wide to permit rotation of said microdevices within said microchannels but sufficiently narrow to prevent said microdevices from forming a chain when the major axis of said microdevices is substantially perpendicular to the major axis of said microchannels wherein the said microdevices are subjected to an applied magnetic field.

In preferred embodiments, the microdevices are manipulated to be "flat" or "substantially flat" in the microchannels so that the photorecognizable patterns on the microdevices can be optically detected or analyzed via the optical means in the direction substantially-normal to the plane defined by the microchannel length and width. In preferred embodiments, the height of the microchannels and/or the constraint on the microdevices by a magnetic field should be adjusted to prevent the microdevices from standing up within the microchannels. In a specific embodiment, the height of the microchannels is less than about 70% of the major axis of the microdevices.

The microchannel array can further comprise a staging area or loading area where the microdevices can be introduced into and/or an output area or an outlet channel where the microdevices may be removed from the microchannel array. The microchannel array can also further comprise a magnetic field generating means capable of generating a magnetic field suitable for manipulating the microdevices into, within and/or out of the microchannel array, or rotating the microdevices within the microchannel array. Any suitable magnetic field generating means can be used. For example, the magnetic field generating means can comprise a permanent magnet, a mobile permanent magnet, an electromagnetic unit, a ferromagnetic material or a microelectromagenetic unit. The magnetic field generating means can be located at any suitable location, e.g., below, within, above and/or near the microchannel array.

C. Methods for Forming a Microdevice Array

In still another aspect, the present invention is directed to a method for forming a microdevice array, which method comprises: a) providing a plurality of microdevices, each of the microdevices comprising a magnetizable substance and a photorecognizable coding pattern, wherein said microdevices have a preferential axis of magnetization; b) providing a microchannel array comprising a plurality of microchannels, said microchannels are sufficiently wide to permit rotation of said microdevices within said microchannels but sufficiently narrow to prevent said microdevices from forming a chain when the major axis of said microdevices is substantially perpendicular to the major axis of said microchannels wherein said microdevices are subjected to an applied magnetic field; c) introducing said plurality of microdevices into said plurality of microchannels; and d) rotating said microdevices within said microchannels by a magnetic force, whereby the combined effect of said magnetic force and said preferential axis of magnetization of said microdevices substantially separates said microdevices from each other.

In preferred embodiments, the microdevices are manipulated to be "flat" or "substantially flat" in the microchannels so that the photorecognizable patterns on the microdevices can be optically detected or analyzed via the optical means in the direction substantially-normal to the plane defined by the microchannel length and width. In preferred embodiments, the height of the microchannels and/or the constraint on the microdevices by a magnetic field should be adjusted to prevent the microdevices from standing up within the microchannels. In a specific embodiment, the height of the microchannels is less than about 70% of the major axis of the microdevices.

The microdevices can be introduced into the microchannels by any suitable force. For example, the microdevices can be introduced into the microchannels by a magnetic force, a fluidic force or a combination thereof. There are multiple methods for introducing or loading the microdevices into the channels. In one example, the microdevices are in the form of the MicroDisks, which have two major surfaces and a small dimension (small thickness) between the two major surfaces. MicroDisks are placed in the loading area near the inlet to the microchannels or channels. A small Neodymium magnet at the outlet end of the channel is used to draw the MicroDisks into the channel. The magnet is rotated to facilitate movement of the MicroDisks into the channels. In one experiment, the MicroDisk's major surfaces are of dimensions of 90 $\mu$m by 70 $\mu$m and the MicroDisks are several $\mu$m thick. Using the above-described procedure, it was possible to completely fill five 2 cm long channels (channel widths ranging from 120–160$\mu$) with 90×70$\mu$ MicroDisks (containing magnetic strips (or bars) with the "3-finger" pattern) in less than 3 minutes. The length, width and height directions of the magnetic strips or bars correspond, respectively to, the length, width and height directions of the MicroDisks. Since the rate-limiting step in the loading or filling process is the MicroDisks moving along the length of the channel, the number of channels can be increased without significantly affecting loading or filling time, e.g. two hundred 2 cm long channels can be filled with about 50,000 MicroDisks within a 3-minute time-period using this procedure. Channels loaded in this manner may be overloaded such that when the direction of the applied external magnetic field is perpendicular to the channel the "perpendicularly arrayed" MicroDisks will be overlapping. Overlaps can be relieved by alternating the direction of the applied external magnetic field between perpendicular and parallel several times. This causes the "chains" to lengthen. In this example, preferably, MicroDisks are introduced into the channels or microchannels so that the height direction of the MicroDisks is substantially aligned with the height direction of the microchannels or channels. Preferably, MicroDisks that have been loaded and/or arrayed into the channels or microchannels are lying flat on the surface of the microchannels.

In another example, the microdevices are in the form of the MicroDisks, which have two major surfaces and a small dimension (small thickness) between the two major surfaces. MicroDisks are loaded into the microchannels or channels exactly as described in above example with the addition of a steady flow-rate of liquid through the channels to increase the efficiency of channel loading. In this example, preferably, MicroDisks are introduced into the channels or microchannels so that the height direction of the MicroDisks is substantially aligned with the height direction of the microchannels or channels. Preferably, MicroDisks that have been loaded and/or arrayed into the channels or microchannels are lying flat on the surface of the microchannels.

In still another example, the microdevices are in the form of the MicroDisks, which have two major surfaces and a small dimension (small thickness) between the two major surfaces. The MicroDisks comprises magnetic strips or bars, whose length, width and height directions correspond, respectively, to the length, width and height directions of the MicroDisks. MicroDisks are placed in the loading area near the inlet to the channels. A large Neodymium magnet at the outlet end of the channel is used to draw the MicroDisks into the channel. The magnet field from this magnet is perpendicular to the channels. A small Neodymium magnet is placed above or below the inlet to the channels and rotated to facilitate movement of the MicroDisks into the channels. A steady flow-rate of liquid through the channels increases the efficiency of channel loading. MicroDisks are loaded in their final "perpendicularly arrayed" form (preferential axis of magnetization perpendicular to the long (or major) axis of the channel), minimizing channel overloading and providing a more uniform arraying pattern. The method of loading or arraying the MicroDisks in this example will result in the magnetic bars within or on the MicroDisks being perpendicular to the channel after the MicroDisks are loaded into the channels or microchannels, i.e. the length direction of the magnetic strips or bars (i.e. the length direction of the MicroDisks) will be normal or substantially normal to the length direction of the microchannels. In this example, preferably, MicroDisks are introduced into the channels or microchannels so that the height direction of the MicroDisks is substantially aligned with the height direction of the microchannels or channels. Preferably, MicroDisks that have been loaded and/or arrayed into the channels or microchannels are lying flat on the surface of the microchannels.

The microdevices or MicroDisks can be introduced into the microchannels at any suitable angle. For example, the microdevices can be introduced into the microchannels by a magnetic field at a direction such that the angle between the major axis of the microdevice and the microchannel is about less than 45 degrees. The direction of the magnetic field will affect the orientation of the microdevices or MicroDisks and affect the direction of the major axis of the microdevice. Normally, when the microdevices can freely rotate or re-orientate, the preferential axis of magnetization is substantially aligned with the applied magnetic field. For microdevice or MicroDisk whose preferential axis of magnetization is the same as, or substantially aligned with, the major axis of the microdevice, then the major axis of the microdevice is substantially aligned with the applied magnetic field. It is thus possible to introduce the microdevices into the microchannels by a magnetic field at appropriate directions so that the major axis of the microdevice is angled with respect to the length direction of the microchannels at degrees less than 45 degree. Preferably, the microdevices are introduced into the microchannels by a magnetic field at a direction such that the angle between the major axis of the microdevice and the microchannel is about less than 40, 35, 30, 25, 20, 15, 10, 5 or 0 degrees.

The present method can further comprise a step of breaking a chain formed among the microdevices prior to or concurrent with introducing the microdevices into the microchannels. This can be accomplished by any suitable methods, e.g., rotating the direction of magnetic field between the major and minor axis of the microdevices.

Preferably, after microdevices or MicroDisks are loaded and/or filled into the channels or microchannels, microdevices or MicroDisks are lying flat on the surface of the microchannels. The microdevices or MicroDisks can be rotated within the microchannels for any suitable degrees provided that the rotation is sufficient to substantially separate the microdevices or MicroDisks from each other. The separation can be achieved by a single rotation of a larger degree or by multiple rotations for smaller degrees. Preferably, the microdevices or MicroDisks are rotated at least 45 degrees. More preferably, the microdevices or MicroDisks are rotated 90 degrees.

In a specific embodiment, at least one of the microdevices binds to a moiety and the method is used to manipulate said moiety. In another specific embodiment, a plurality of the microdevices bind to a plurality of moieties and the method is used to manipulate said plurality of moieties. The present method can be used for any suitable manipulation of a moiety, e.g., transportation, focusing, enrichment, concentration, aggregation, trapping, repulsion, levitation, separation, fractionation, isolation and linear or other directed motion of the moiety. In still another specific embodiment, the present method can further comprise a step of assessing the identity of the manipulated moiety by photoanalysis of the photorecognizable coding pattern on the microdevice to which the moiety binds. Assessment of the identity of the manipulated moiety may involve obtaining an index, ratio, percentage, visual or other value indicative of the identity of the manipulated moiety. In still another specific embodiment, the present method can further comprise a step of assessing the quantity of the manipulated moiety by further quantitative means for analyzing the amount of the manipulated moiety on the microdevice. The assessment of the quantity of the manipulated moiety may involve obtaining a number, an index, or other value indicative of the amount or quantity or the concentration of the manipulated moiety. In yet another specific embodiment, the present method can further comprise a step of collecting the microdevice to which the moiety binds through an outlet channel. The present method can further comprise a step of recovering the moiety from the collected microdevice.

In yet another aspect, the present invention is directed to a method for forming a microdevice array, which method comprises: a) providing a plurality of microdevices, each of the microdevices comprising a magnetizable substance and a photorecognizable coding pattern, wherein said microdevices have a preferential axis of magnetization, on a surface suitable for rotation of said microdevices; and b) rotating said microdevices on said surface by a magnetic force, whereby the combined effect of said magnetic force and said preferential axis of magnetization of said microdevices substantially separates said microdevices from each other.

In yet another aspect, the present invention is directed to a method for forming a microdevice array, which method comprises: a) providing a plurality of the microdevices, each of the microdevices comprising a magnetizable substance and a photorecognizable coding pattern, and having a preferential axis of magnetization; b) introducing said plurality of microdevices onto a surface; and rotating said microdevices by a magnetic force to form chains and clusters, whereby the combined effect of said magnetic force and said preferential axis of magnetization of said microdevices substantially separates the microdevices from each other. In an embodiment of the arraying method, the microdevices are introduced onto the surface in a liquid suspension. The microdevice suspension can be added to the surface by a variety of methods, such as via micropieppetting, or pumping into the microchanels that are formed on the surface. In another embodiment of the methods, the surface may comprise grooves with width dimensions substantially narrower than that of the microdevice. After the microdevice are arrayed on the surface, the liquid in which the microdevices are suspended may be removed via the grooves on the surfaces by various methods such as suction or pumping out.

The present methods can be used for analyzing, isolating, manipulating or detecting any types of moieties when the moieties are involved in certain processes, such as physical, chemical, biological, biophysical or biochemical processes, etc., in a chip format or non-chip format. Moieties can be cells, cellular organelles, viruses, molecules or an aggregate or complex thereof. Moieties can be pure substances or can exist in a mixture of substances wherein the target moiety is only one of the substances in the mixture. For example, cancer cells in the blood from leukemia patients, cancer cells in the solid tissues from patients with solid tumors and fetal cells in maternal blood from pregnant women can be the moieties to be isolated, manipulated or detected. Similarly, various blood cells such as red and white blood cells in the blood can be the moieties to be isolated, manipulated or detected. DNA molecules, mRNA molecules, certain types of protein molecules, or all protein molecules from a cell lysate can be moieties to be isolated, manipulated or detected.

Non-limiting examples of cells include animal cells, plant cells, fungi, bacteria, recombinant cells or cultured cells. Animal, plant cells, fungus, bacterium cells to be isolated, manipulated or detected can be derived from any genus or subgenus of the Animalia, Plantae, fungus or bacterium kingdom. Cells derived from any genus or subgenus of ciliates, cellular slime molds, flagellates and microsporidia can also be isolated, manipulated or detected. Cells derived from birds such as chickens, vertebrates such fish and mammals such as mice, rats, rabbits, cats, dogs, pigs, cows, ox, sheep, goats, horses, monkeys and other non-human primates, and humans can be isolated, manipulated or detected by the present methods.

For animal cells, cells derived from a particular tissue or organ can be isolated, manipulated or detected. For example, connective, epithelium, muscle or nerve tissue cells can be isolated, manipulated or detected. Similarly, cells derived from an accessory organ of the eye, annulospiral organ, auditory organ, Chievitz organ, circumventricular organ, Corti organ, critical organ, enamel organ, end organ, external female genital organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl can be isolated, manipulated or detected. Preferably, cells derived from an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc can be isolated, manipulated or detected. Further, cells derived from any plants, fungi such as yeasts, bacteria such as eubacteria or archaebacteria can be isolated, manipulated or detected. Recombinant cells derived from any eucaryotic or prokaryotic sources such as animal, plant, fungus or bacterium cells can also be isolated, manipulated or detected. Cells from various types of body fluid such as blood, urine, saliva, bone marrow, sperm or other ascitic fluids, and subfractions thereof, e.g., serum or plasma, can also be isolated, manipulated or detected.

Isolatable, manipulatable or detectable cellular organelles include nucleus, mitochondria, chloroplasts, ribosomes, ERs, Golgi apparatuses, lysosomes, proteasomes, secretory vesicles, vacuoles or microsomes. Isolatable, manipulatable or detectable viruses include intact viruses or any viral structures, e.g., viral particles, in the virus life cycle that can be derived from viruses such as Class I viruses, Class II viruses, Class III viruses, Class IV viruses, Class V viruses or Class VI viruses.

Isolatable, manipulatable or detectable molecules can be inorganic molecules such as ions, organic molecules or a complex thereof. Non-limiting examples of ions include sodium, potassium, magnesium, calcium, chlorine, iron, copper, zinc, manganese, cobalt, iodine, molybdenum, vanadium, nickel, chromium, fluorine, silicon, tin, boron or arsenic ions. Non-limiting examples of organic molecules include amino acids, peptides, proteins, nucleosides, nucleotides, oligonucleotides, nucleic acids, vitamins, monosaccharides, oligosaccharides, carbohydrates, lipids or a complex thereof.

Any amino acids can be isolated, manipulated or detected by the present methods. For example, a D- and a L-amino-acid can be isolated, manipulated or detected. In addition, any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V) can be isolated, manipulated or detected.

Any proteins or peptides can be isolated, manipulated or detected by the present methods. For example, membrane proteins such as receptor proteins on cell membranes, enzymes, transport proteins such as ion channels and pumps, nutrient or storage proteins, contractile or motile proteins such as actins and myosins, structural proteins, defense protein or regulatory proteins such as antibodies, hormones and growth factors can be isolated, manipulated or detected. Proteineous or peptidic antigens can also be isolated, manipulated or detected.

Any nucleic acids, including single-, double and triple-stranded nucleic acids, can be isolated, manipulated or detected by the present methods. Examples of such nucleic acids include DNA, such as A-, B- or Z-form DNA, and RNA such as mRNA, tRNA and rRNA.

Any nucleosides can be isolated, manipulated or detected by the present methods. Examples of such nucleosides include adenosine, guanosine, cytidine, thymidine and uridine. Any nucleotides can be isolated, manipulated or detected by the present methods. Examples of such nucleotides include AMP, GMP, CMP, UMP, ADP, GDP, CDP, UDP, ATP, GTP, CTP, UTP, dAMP, dGMP, dCMP, dTMP, DADP, dGDP, dCDP, dTDP, dATP, dGTP, dCTP and dTTP.

Any vitamins can be isolated, manipulated or detected by the present methods. For example, water-soluble vitamins such as thiamine, riboflavin, nicotinic acid, pantothenic acid, pyridoxine, biotin, folate, vitamin $B_{12}$ and ascorbic acid can be isolated, manipulated or detected. Similarly, fat-soluble vitamins such as vitamin A, vitamin D, vitamin E, and vitamin K can be isolated, manipulated or detected.

Any monosaccharides, whether D- or L-monosaccharides and whether aldoses or ketoses, can be isolated, manipulated or detected by the present methods. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any lipids can be isolated, manipulated or detected by the present methods. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

D. Methods for Synthesizing a Library and uses thereof

In another aspect, the present invention is directed to a method for synthesizing a random library, which method comprises: a) providing a plurality of microdevices, each of said microdevices comprises a magnetizable substance and a unique photorecognizable coding pattern, wherein each of said microdevices has a preferential axis of magnetization and wherein said unique photorecognizable coding pattern on each of said microdevices corresponds to an entity to be synthesized on each of the said microdevices; and b) synthesizing said entities on said microdevices, wherein said microdevices are identified after each synthesis cycle according to said unique photorecognizable coding patterns, whereby a library is synthesized, wherein each of said microdevices contains an entity that corresponds to said unique photorecognizable coding pattern on each of the said microdevices and the sum of said microdevices collectively contains a plurality of entities. A library that is synthesized according to the above method is also provided.

In yet another aspect, the present invention is directed to a method for synthesizing a library of predetermined sequence, which method comprises: a) providing a plurality of microdevices, each of said microdevices comprises a magnetizable substance and a photorecognizable coding pattern, wherein said microdevices have a preferential axis of magnetization and wherein said photorecognizable coding pattern corresponds to an entity to be synthesized on said microdevice; and b) synthesizing said entities on said microdevices, wherein said microdevices are sorted after each synthesis cycle according to said photorecognizable coding patterns, whereby a library is synthesized, wherein each of said microdevices contains an entity that corresponds to a photorecognizable coding pattern on said microdevice and the sum of said microdevices collectively contains a plurality of entities that is predetermined before the library synthesis. A library that is synthesized according to the above method is also provided.

The microdevices can be sorted by any suitable methods. For example, the microdevices can be sorted through a microchannel array comprising a plurality of microchannels, said microchannels are sufficiently wide to permit rotation of said microdevices within said microchannels but sufficiently narrow to prevent said microdevices from forming a chain when the major axis of said microdevices is substantially perpendicular to the major axis of said microchannels, via a combined effect of a magnetic force and the preferential axis of magnetization of the microdevices that substantially separates the microdevices from each other. The height of the microchannels and/or the constraint on the microdevices by a magnetic field should be adjusted to prevent the microdevices from standing up within the microchannels. In a specific embodiment, the height of the microchannels is about less than 70% of the major axis of the microdevices. After the microdevices are arrayed into the microchannels, photoanalysis of microdevices is performed to determine photorecognizable coding (or encoding) pattern of individual microdevice. A method that can handle individual microdevice is used to manipulate individual microdevice and to sort them to different regions/locations/reaction chambers according to their photorecognizable pattern. For example, a microelectromagnetic needle that can generate magnetic field at a fine tip-end of the needle can be used to pick up individual microdevice from their arrayed channels (in this case, the channels have to be open on the top side) and move and send/dispense individual microdevices to different locations/regions/reaction chambers. In another example, microdevices are moved out from the microchannels by, e.g., a combination of magnetic forces and fluidic forces, and at the outlet region of the channel, microdevices can be sent to different locations by the control of magnetic forces and/or fluidic forces.

Sorting can also be accomplished through the use of magnetic force to specifically capture desired grouping of microdevices after each step of the synthesis and deposit them into the appropriate reaction vessel. Microdevices can be arrayed using a photoresist to form either the top or bottom surface of the arraying chamber. When exposed to light of the appropriate wavelength the photoresist in the illuminated regions can be dissolved exposing the Microdevices in those locations and allowing them to be removed by magnetic force. A programmable digital micromirror array (e.g. "Maskless fabrication of light-directed oligonucleotides microarrays using a digital micromirror array" by Singh-Gasson et al. *Nature Biotechnology*, 17:974–978 (1999)) or similar maskless array synthesizer device could be used to direct the light.

An alternative and preferred method of sorting utilizing magnetic force is to use sorting channels. As discussed above, microdevices having a preferential axis of magnetization when arrayed in a channel in the presence of a magnetic field will align and separate due to repulsive magnetic force and can be drawn through liquid filled channels in a "perpendicularly arrayed" form (preferential axis of magnetization perpendicular to the long axis of the channel). A sufficient increase in surface tension will prevent movement of the microdevice. Such an effect can be generated by creating an appropriate liquid-liquid (immiscible liquids such as hexane and water) or gas-liquid interface. For example consider an arraying channel separated from a series of sorting channels by a microvalve (the design, manufacture, and use of such valves are well known to those practiced in the art). Through an appropriately positioned orifice near the end of the arraying channel a bubble can be introduced between the final and the penultimate microdevice. Opening of the valve and application of a magnetic force will result in only the final microdevice being drawn through the channel into the sorting channels, others microdevices will remain trapped behind the bubble. The valve is then closed and the single disk in the sorting channel can be directed using magnetic and/or fluidic force to and/or other physical force (e.g. dielectrophoresis force) the appropriate reaction vessel. Application of fluidic force (pumping liquid) drives the bubble out through an appropriately placed outlet at the end of the channel allowing the microdevices to advance and the sorting process is then repeated. The size of orifices for gas delivery and removal must be significantly smaller than the microdevices. An alternative and potentially more rapid system would be to introduce bubbles between all of the microdevices within a channel and to adjust the magnetic field and fluidic force such that the microdevices move in a segmented fashion through the channel. This is analogous to the segmented fluid flow approach widely used by Technicon International, Ltd. to prevent peak broadening (e.g., U.S. Pat. Nos. 2,797,149 and 3,109,713). A third parameter in addition to magnetic and fluidic force which can be adjusted to insure smooth segmented flow of microdevices is the surface tension of the liquid(s) which can be regulated by the use the appropriate solvents or additives (e.g. surfactants). The ability to alter surface tension by choice of solvents is known to anyone trained in the art.

In another example, microdevices can be sorted using the apparatuses (i.e.: particle switches) that can switch and manipulate particles. U.S. patent application Ser. No. 09/678,263, filed on Oct. 3, 2000, titled "Apparatus for switching and manipulating particles and methods of use thereof" describe several types of devices and apparatuses for switching, sorting and manipulating particle. The patent application Ser. No. 09/678,263 is incorporated by reference in its entirety. The devices and apparatuses and the methods of their use can be applied for sorting microdevices of present invention. For example, traveling-wave dielectrophoresis can be used as a mechanism for sorting particles via a particle-switching device. The particle switching device comprises at least three sets of electrodes which are electrically independent from each other. The three or more sets of electrodes are capable of generating respective traveling-wave dielectrophoresis (twDEP) forces on particles to move the particles along respective branches when the electrodes in each set of electrodes are connected to out-of-phase signals, and said branches are interconnected at a common junction to permit the twDEP forces to route particles from one of the branches to another of the branches. The end (other than the common junction of the branches) of each branch may be used for the inlet (input) and/or outlet (output) ports. Thus, in this example, the particle sorting device has at least three inlet (input)/outlets (outputs). Consider an example where the particle sorting device has one inlet and two outlet ports. Microdevices of the present invention can be fed into the inlet port and then transported along the branches within the particle sorting device to be outputted in one of the two outlets, depending on the electrical voltage signals applied to the electrodes. More importantly, for a given microdevice of the present invention, it is possible to first perform photo-analysis to determine the photorecognizable coding pattern on the microdevice and then according to its coding pattern, appropriate electrical signals can be applied to the electrodes within the particle sorting device so that the microdevice can be transported and sorted to one of the two outlet ports. An array of such particle sorting devices can be used for sorting microdevices into more than two outlet ports (or more than two output points/positions). Examples of such multiple particle-sorting-device used in an array format are also disclosed in the U.S. patent application Ser. No. 09/678,263, which is incorporated by reference in its entirety.

Microdevices can also be sorted using a flow system, which has one inlet port and multiple outlet ports. The flow system can transport microdevices from the inlet port to any one of multiple outlet ports. Each microdevice can be flown through an optical decoder (in the flow system), which can identify the photorecognizable coding pattern of the microdevice, and is then directed to different outlet ports according to the identified coding pattern on the microdevice by changing the fluid flow patterns in the flow system.

Any other sorting method that can sort microdevices according to their photorecognizable coding patterns can be used.

Any number of suitable entity(ies) can be synthesized on a single microdevice. For example, a single entity or a plurality of entities can be synthesized on a single microdevice. Preferably, a single entity is synthesized on a single microdevice.

The present method can be used to synthesize any kind of library. For example, the synthesized entities can be peptides, proteins, oligonucleotides, nucleic acids, vitamins, oligosaccharides, carbohydrates, lipids, small molecules, or a complex or combination thereof. Preferably, the synthesized library comprises a defined set of entities that are involved in a biological pathway, belongs to a group of entities with identical or similar biological function, expressed in a stage of cell cycle, expressed in a cell type, expressed in a tissue type, expressed in an organ type, expressed in a developmental stage, entities whose expression and/or activity are altered in a disease or disorder type or stage, or entities whose expression and/or activity are altered by drug or other treatments.

In a specific embodiment, the synthesized library comprises a defined set of nucleic acid, e.g., DNA or RNA, fragments such as a defined set of nucleic acid fragments that cover an entire genome, e.g., the entire human genome sequence. Preferably, each of the nucleic acid fragments in the synthesized library comprises at least 2, 3, 5, 10, 15, 20, 25, 50, 75, 100, 200, or 500 nucleotides.

In another specific embodiment, the synthesized library comprises a defined set of protein or peptide fragments such as a defined set of protein or peptide fragments that cover protein or peptide sequences encoded by an entire genome, e.g., the entire human genome sequence. Preferably, each of the protein or peptide fragments in the synthesized library comprises at least 2, 3, 5, 10, 15, 20, 25, 50, 75, 100, 150, 200, 300, 400 or 500 amino acid residues.

In still another specific embodiment, a library that is synthesized according to the above-described method is provided.

E. Preferred Embodiments

Figure 2:
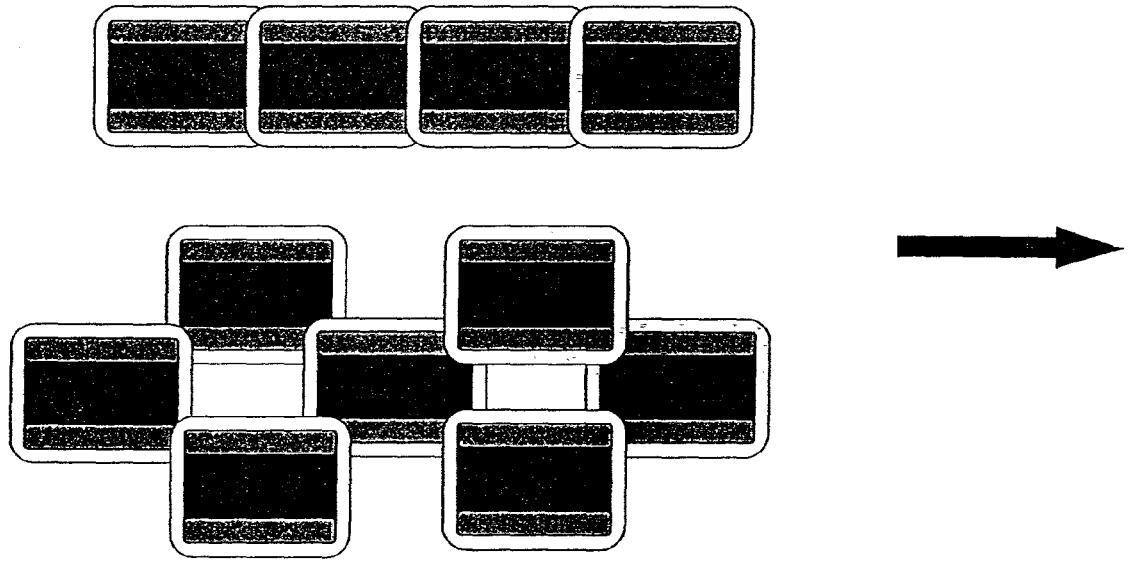
FIG. 2 illustrates examples of possible arrangements of multiple MicroDisks constrained to a surface in the presence of a magnetic field whose direction is indicated by the arrow.
Figure 3:
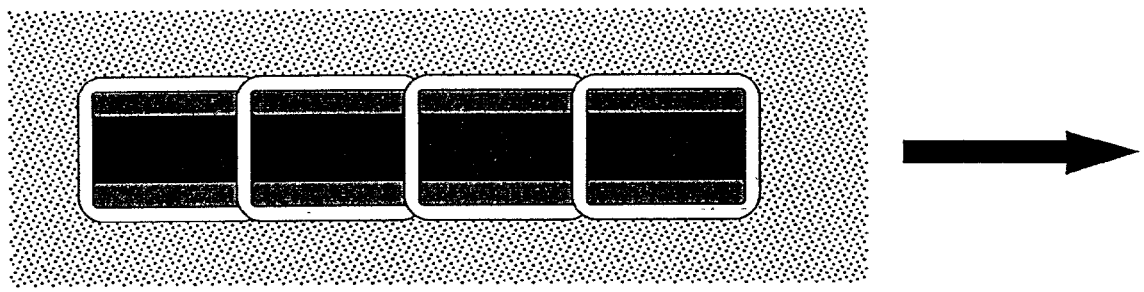
FIG. 3 illustrates a short chain of MicroDisks constrained to a surface and further constrained in a channel while in the presence of a magnetic field whose direction is indicated by the arrow.
Figure 4:
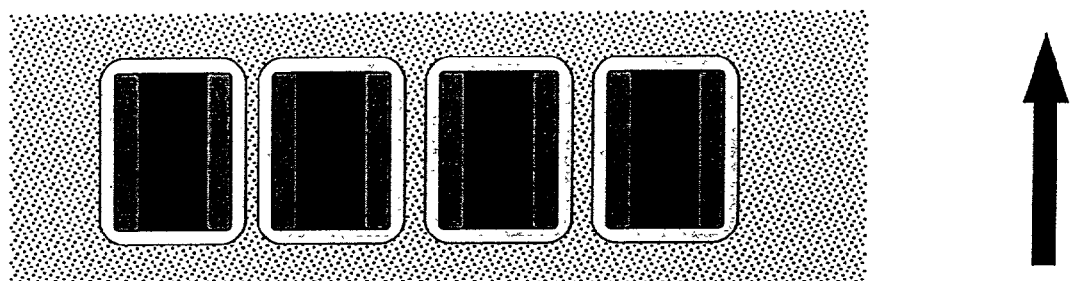
FIG. 4 illustrates the same short chain of MicroDisks shown in FIG. 3 after the external magnetic field has been rotated by 90 degrees as indicated by the arrow.

In one specific embodiment, the present invention is directed toward a method for arraying microdevices (or MicroDisks) in predetermined geometries using magnetic forces. A MicroDisk is a microfabricated particle ranging in size from $1-1000\mu$ on a side and containing one or more strips or bars of magnetic material. These bars must have the property of having a preferential axis of magnetization. Such a property is a consequence of the physical geometry of the magnetic material and, typically, will consist of a thin film (generally less than $1\mu$) bar having a length to width ratio of greater than 3. Typically, the preferential axis of magnetization of a bar is its major axis. An example of a MicroDisk containing two magnetic strips or bars is shown in FIG. 1. For example in the presence of a magnetic field as indicated by the arrow, the MicroDisks will orient or rotate so that the preferential axis of magnetization will be parallel or substantially parallel to the field. For such MicroDisks, the preferential axis of magnetization is aligned with its major axis, or is its major axis. If not spatially constrained, MicroDisks will form chains and clusters as shown in FIG. 2 (the arrow indicating the direction of applied magnetic field). Chains may be constrained to a channel as shown in FIG. 3. A 90-degree rotation of the magnetic field once the MicroDisk chains are constrained in a channel will cause the MicroDisks to rotate and separate as shown in FIG. 4. The process of steps illustrated in FIGS. 2–4 comprises "magnetic arraying".

The first step in the process, formation of chains and clusters, occurs spontaneously in the presence of a magnetic field. In order to be moved into channels clusters must be disrupted. This process is accomplished by rotating the magnetic field. Guiding posts (discussed below in the description of microchannels) may be used to provide pivot points for the rotating clusters and chains, thereby facilitating their rearrangement. A series of properly constructed posts leads to the creation of chains of narrow width. The chain may be wider than the width of a single MicroDisk.

Chains can then be moved into channels using magnet force or fluidic force or a combination of the two. Chains will move along lines of increasing magnetic field strength. If the length-direction of the chain (which is substantially aligned with the preferential axis of magnetization of MicroDisk) aligns with or substantially aligns with the movement direction, then a smaller hydrodynamic dragging resistance is exerted on the chains, leading to a faster movement. On the other hand, it appears that, at least for individual MicroDisks, larger magnetic force is exerted on the MicroDisks if the preferential axis of magnetization is perpendicular or substantially perpendicular to the movement direction along which the magnetic field is increased in magnitude. For these reasons, the chains move most efficiently when the length-direction of the chain is at angles less than 90 degree to the direction along which the magnetic field is increased in magnitude, typically around 45 degrees, although the chains can also move at other degrees. Such magnetic field gradients can be generated by large permanent magnets or electromagnets as well as by a series of small electromagnets either within or adjacent to the surface of the channels. Once the MicroDisks are in the channel rotation of the magnetic field so that it is perpendicular to the MicroDisks chain (as well as the channel) results in the individual MicroDisks rotating to align with the field.

Selection of optimal dimensions for the MicroDisks and channels is important. The amount of overlap of MicroDisks in the chains is dependent on the shape of the magnetic strips or bars within or on the MicroDisk and the thickness of the MicroDisk. In the example shown in FIG. 1, disks would be expected to overlap by 20–30% when in the chain configuration. By having a length to width ratio of 1.22 ($90\mu/70\mu$) when the MicroDisks are rotated in the channel, there is no requirement for a significant change in the relative positions of the individual MicroDisk's center of mass within the channel due to the rotation of the magnetic field. By contrast, circular MicroDisks either would remain overlapped or would, as a consequence of magnetic repulsion, spread laterally through channel.

The optimal width of the channel is controlled by two factors. The channel must be wide enough to allow the MicroDisks to rotate, for the example shown in FIG. 1 the diagonal of the MicroDisk is ~114 $\mu$ ($=\sqrt{90^2+70^2}$) hence this is the minimum width. The channel should be narrow enough to prevent two disks from forming a chain when their magnetic bars or their major axis are perpendicular to the axis of the channel when a magnetic field in the direction along the channel with is applied. In the example shown in FIG. 1 where the MicroDisk has a dimension of 90 $\mu$m by 70 $\mu$m for its major surfaces, assuming an overlap of ~30%, the length of two overlapping MicroDisks would be ~153 $\mu$m (=90+90−90×0.3), hence this is the maximum width. For overlaps of 10% or 20%, the corresponding maximum width would be 171 $\mu$m or 162 $\mu$m. Channel height is also important since in a strong magnetic field the MicroDisks will tend to stand upright. When the constraint on the microdevices by a magnetic field alone is sufficient to prevent microdevices from taking such a prohibitive position, the height of the microchannels may become irrelevant in this consideration. The arraying principles discussed above and illustrated in FIGS. 2–4 are dependent on the MicroDisks being constrained to lie flat in a plane. Consequently, the height of the channels should be less than the narrow dimension of the MicroDisks. A MicroDisk having angles of elevation slightly less than 90 degrees with respect to the bottom surface of the microchannel may be stable if the microchannel is covered with a lid or otherwise sealed on the top. The minimum angle of elevation which still permits stable standing of the MicroDisks is dependent on the strength of the magnetic field, the amount of magnetic material and its saturation magnetization, as well as the weight and density of the MicroDisks and the density of the surrounding fluid. While these values can be determined either empirically or through modeling, elevation angles less than 45 degrees would generally result in the Microdisks lying flat in the microchannels. For these reasons, for the MicroDisk shown in FIG. 1 a maximum channel height that prevents the MicroDisk standing up in the channel is ~50$\mu$= (70$\mu$×sin(45)).

Figure 5:
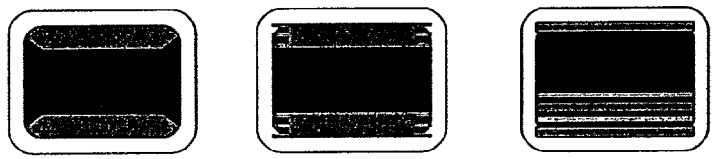
FIG. 5 shows examples of MicroDisks containing different types of magnetic bars.

The shape of the magnetic bars (or magnetic strips) within or on the MicroDisks can be tailored to direct certain types of chains and clusters to form and to alter the amount of overlap between MicroDisks. FIG. 5 shows some examples of other types of bars.

Figure 6:
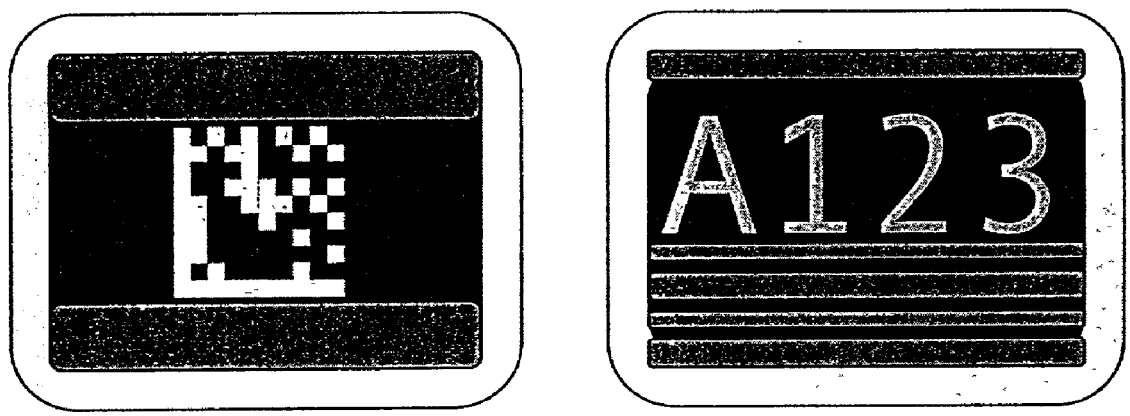
FIG. 6 shows examples of two types of encoding patterns: 2D datamatrix on the left and four character optical character recognition (OCR) on the right.
Figure 7:
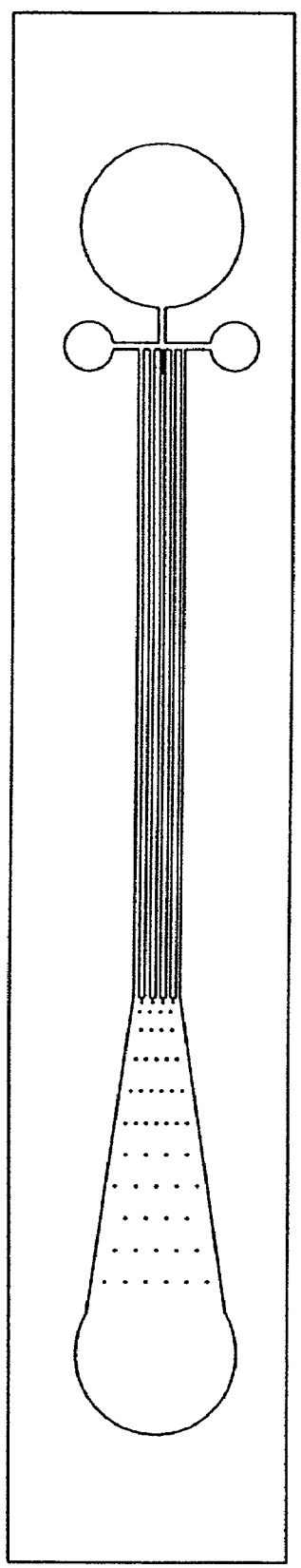
FIG. 7 shows an exemplary microchannel device containing a loading region, guiding posts, microchannels, collection areas and fluidic connections.
Figure 8:
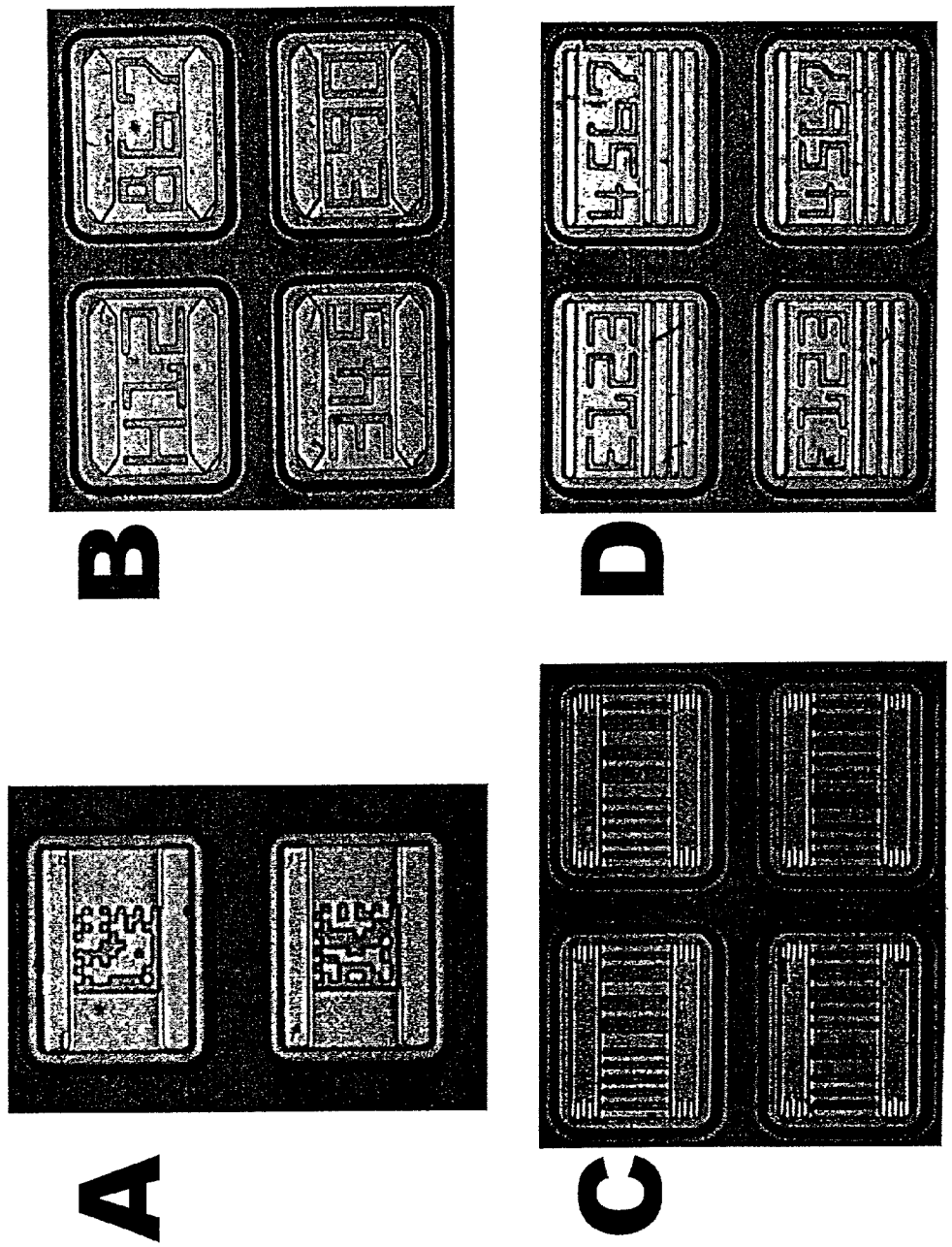
FIG. 8 shows 4 exemplary types of MicroDisks. Images show MicroDisks after fabrication but before release from the wafer. Magnification is ~400×. A—Pair of rectangular magnetic bars, 2D bar code; B—Pair of rectangular magnetic bars with tapered ends, 3-character OCR code; C—Pair of rectangular magnetic bars with "three-fingered" ends; 1D bar code; D—Five rectangular magnetic bars, 4-character OCR code.

MicroDisks can be encoded in a variety of ways to make them individually identifiable. The preferred encoding method is one generated during the fabrication of the MicroDisks such as 2-D bar coding or inclusion of optical character recognition (OCR) characters as shown in FIG. 6.

Encoded MicroDisks can be fabricated using any methods known in the art. A typical MicroDisk as shown in FIG. 1 would consist of four regions. Magnetic bars or strips are shown in light gray. Dark gray region (e.g., made of the material Aluminum, Al) is an encoding region. The surrounding white edge indicates the regions that encapsulate the magnetic bars and encoding region and provide the surface for modification. This edge could be any simple material e.g., silicon, ceramic, metal, etc., though a preferred material is $SiO_2$. These different regions are also located separately along the thickness direction. The magnetic bars and the encoding region are located in the middle, and are encapsulated by the top and bottom layers that correspond to the surrounding white edge.

The magnetic bars within or on the MicroDisks can be constructed out of any magnetic material. Preferentially, they will be constructed out of a material of low magnetorestriction, low remanence, but containing a high saturation magnetization. For example, CoTaZr alloys meet these criteria. Materials of higher remanence, e.g. nickel, are compatible with the magnetic arraying process and may be used. The encoding layer may be constructed out of any non-magnetic material. For example, aluminum, gold, or copper could be used. Unlike encoded beads using fluorescent labels, microfabricated bar codes such as those shown in FIG. 6 have no inherent technological limit to the number of different codes. FIG. 6 shows a 4-digit OCR representation, considering only capital and lower case letters and digits (62 characters) results in over $10^7$ possible unique representations for that type of encoding.

The ability to array allows rapid reading of encoding information on the MicroDisk without the need for complex optics with multiple orientations and flow systems. Arrays are compatible with long-term storage and archiving. However, unlike conventional arrays where all captured molecules are fixed to the same surface, in a MicroDisk array each type of captured molecule is bound to a different surface. Consequently, individual MicroDisks can also be used for sequential methods of analysis. For example, following the initial screening a desired subset of MicroDisks could be reprobed with a different detection molecule or could be subjected to another form of analysis, e.g., sequencing or mass spectroscopy. Capture on a MicroDisk in practical terms corresponds to purification of the captured molecule. Therefore, MicroDisks, when coupled with a sorting technology, can be used to purify moieties, including proteins, DNA, cells, etc.

Another aspect of this invention is directed towards the sorting of MicroDisks. Once inside the channel MicroDisks can be moved either individually or in chains through the channel. These channels can be branched to direct output towards different collection chambers using magnetic force. For example, in the case of DNA synthesis each channel can lead to one of four tubes (A, T, C, or G). Such directional channels could also be used to isolate specific subsets of disks for further analysis (See e.g., U.S. patent application Ser. No. 09/924,428, filed Aug. 7, 2001). Other sorting methods described in Section D could also be used for sorting of MicroDisks.

The term "magnetic bars", in addition to rectangular shapes, includes rod-like shapes as well as slightly irregular shapes that still exhibit a preferential axis of magnetization, e.g., elongated pyramidal shapes. While the examples have been confined to flat particles (MicroDisks), the microdevices of the present invention can have any shape including spherical beads. The simplest microdevice consists of a single magnetic bar that is encoded. This encoding can be created during fabrication e.g., by photolithography or it can be added after fabrication of the bar, e.g., by coupling a fluorophore.

Figure 9:
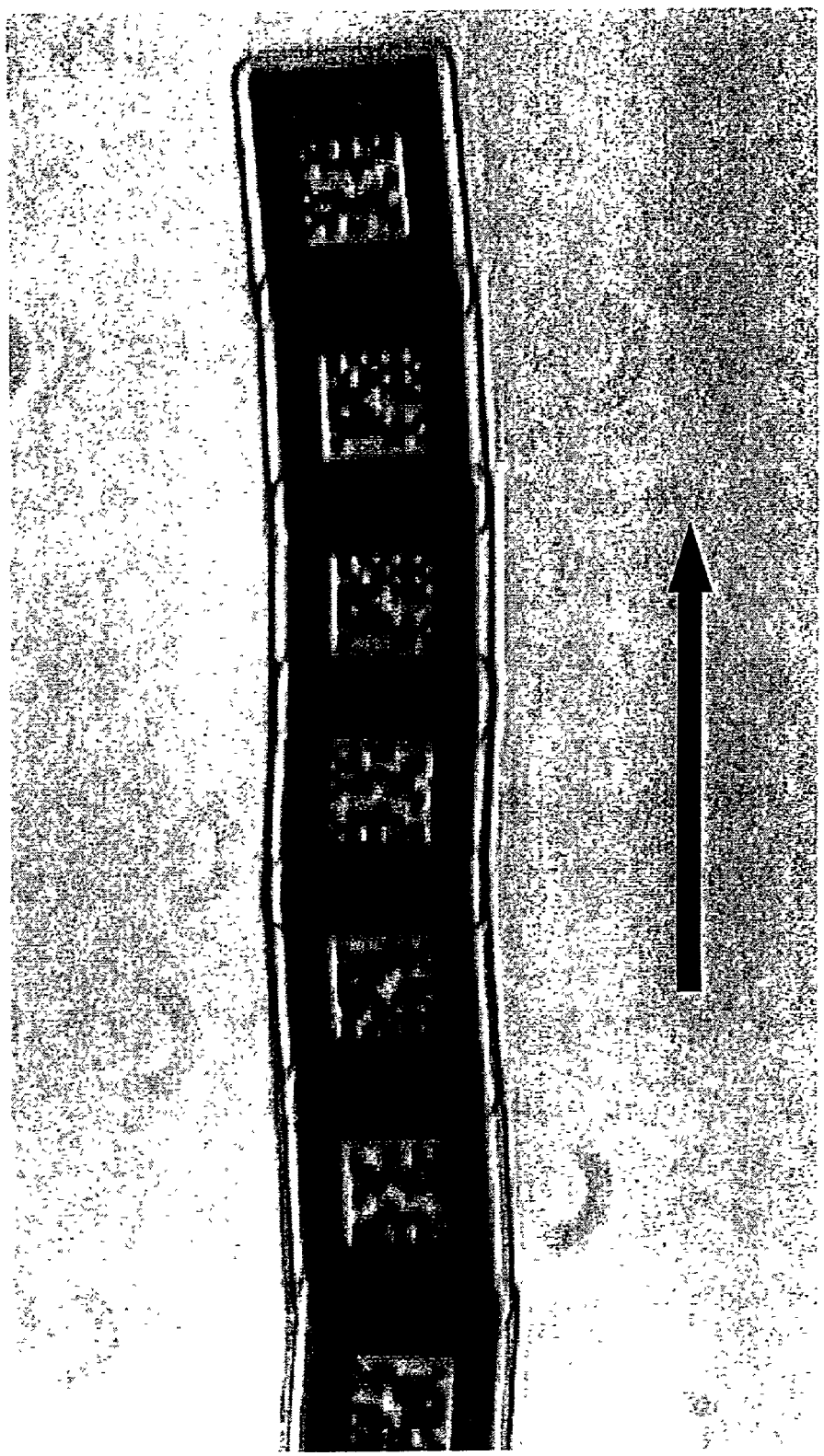
FIG. 9 shows MicroDisks forming linear chains on a glass surface in the presence of a magnetic field whose direction is indicated by the arrow. The 2D bar codes are fully exposed in this chain. Illumination is from below. Magnification is ~400×.
Figure 10:
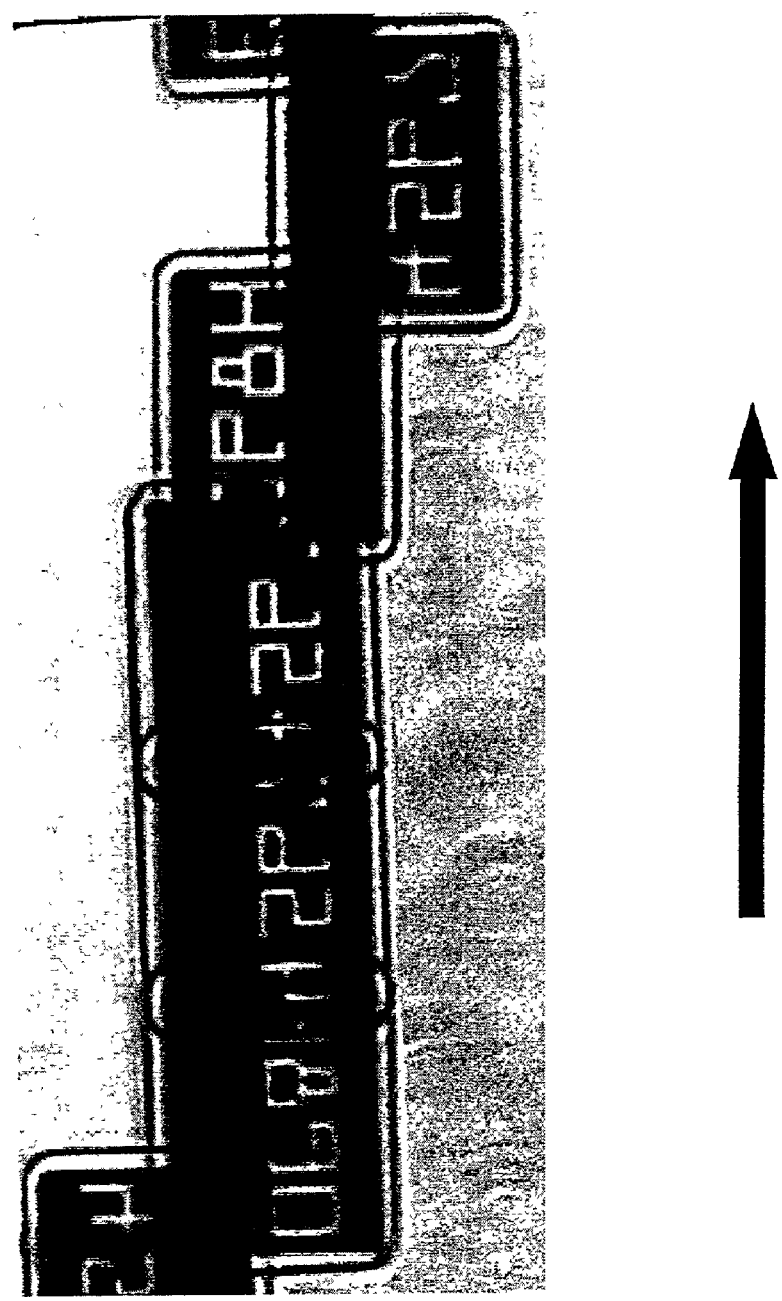
FIG. 10 shows MicroDisks forming chains with some branching on a glass surface in the presence of a magnetic field whose direction is indicated by the arrow. Illumination is from below. Magnification is ~400×.
Figure 11:
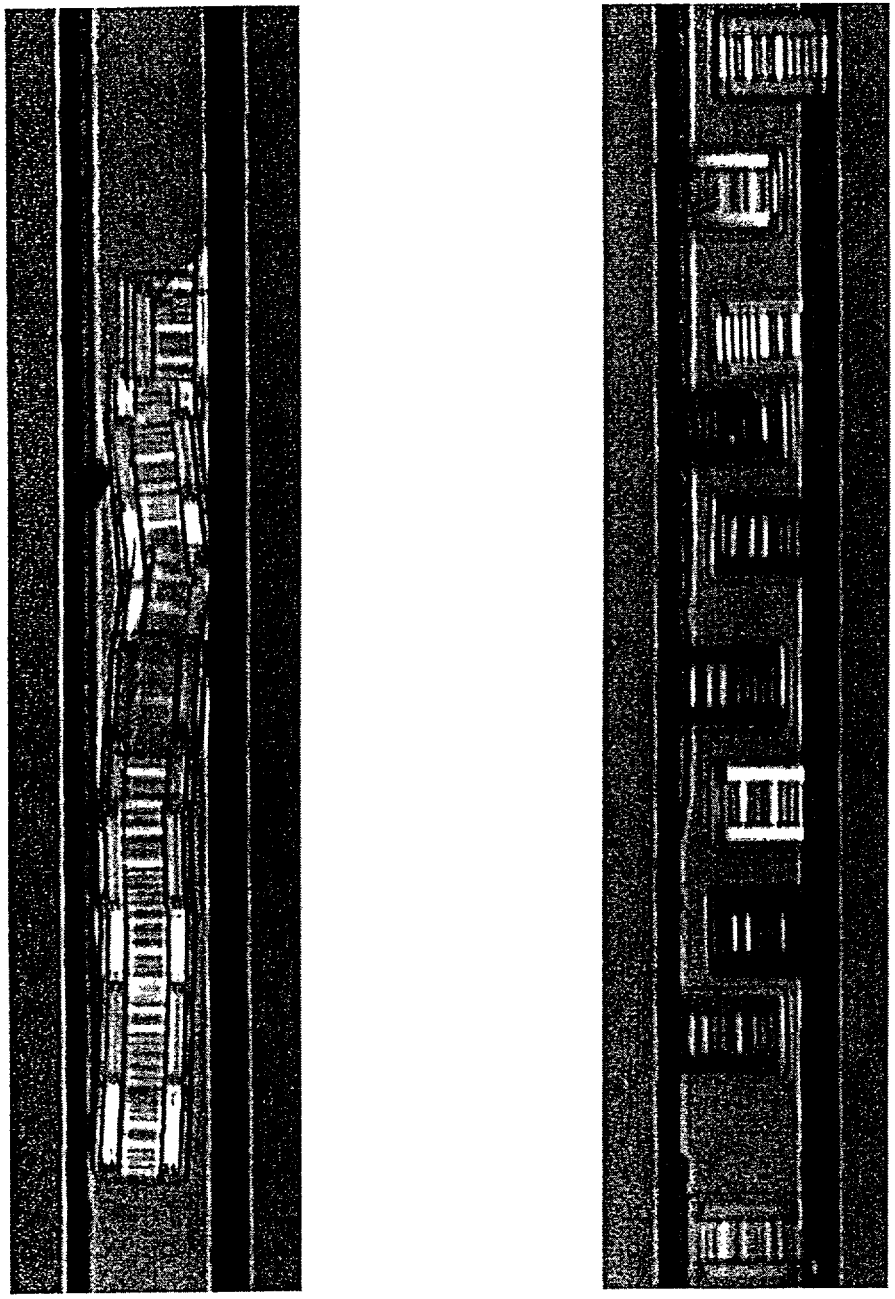
FIG. 11 shows MicroDisks constrained to a $130\mu$ wide channel responding to a magnetic field whose direction is indicated by the arrow. In the upper panel (A), the MicroDisks form a compact chain. Ninety (90)-degree rotation of the magnetic field as shown in the lower panel (B) results in the disks fully separating from each other. Illumination is from above. Magnification is ~160×.

As defined above arraying consists of displaying microdevices in an ordered format such that the encoding pattern is readable. While the preferred form of arraying is for said microdevices to be in channels where their preferential axis of magnetization is perpendicular to the major axis or length axis of the microchannels, the chains of disks shown in FIG. 9 on a glass surface can already be photoanalyzed or detected for the encoding patterns of each individual MicroDisk. Furthermore, while the preferred form of arraying is within channels (as shown in FIGS. 4 and 11), arraying can be carried out on any flat surface e.g., a glass slide (as shown in FIG. 9). In addition, arrays can be effectively formed in chains even if adjacent MicroDisks would overlap. This can be accomplished by employing certain "accessory" MicroDisks that do not contain an encoding pattern and are transparent. By adding an appropriate excess of such transparent, "accessory" MicroDisks to the mixture of encoded MicroDisks before chain formation, the probability of two encoded MicroDisks being adjacent in the chain will be very small. Thus, by simply forming chains of MicroDisks using a magnetic field, we can effectively achieving the arraying of the encoded MicroDisks.

While arraying is generally considered a static process, this need not be the case. For example, particles can be moved through channels and the encoding pattern and other information be read. The encoding pattern and other information can be read by any suitable sorting instruments e.g., FACS machines, while sorting is carried out.

In addition to enabling arraying, microdevices with a preferential axis of magnetization are able to rotate in a controlled manner within a channel in response to changes in the direction of the external applied magnetic field. This rotation facilitates mixing, thereby enhancing reaction kinetics and solution uniformity.

F. EXAMPLES

Protein Profiling

Encoded MicroDisks bearing a $SiO_2$ surface are coated using a silane to provide activatable functional groups, e.g. coating with 3-aminoproplytrimethoxysilane to provide an amine surface. The functional groups are activated for coupling e.g. an amine surface is activated using N-hydroxysulfosuccinimide and 1-ethyl-3-(3-dimethylaminopropyl) carbodiimide and capture antibodies are covalently linked to the surface through primary amino groups. Many such encoded MicroDisks, each containing a different capture antibody, can be made in this manner. Antibody-containing MicroDisks are then incubated with a sample containing antigens (or proteins) recognized by the capture antibodies and biotinylated detection antibodies that recognize those same antigens (or proteins). After a suitable incubation time, fluorescently labeled streptavidin is added and after further incubation, the MicroDisks are arrayed and subjected to analysis on an optical reader to detect the encoding pattern and on a fluorescence reader to determine the level of bound antigen (or protein).

mRNA/cDNA Profiling

Encoded MicroDisks encapsulated in $SiO_2$ are modified using a silane to generate an aldehyde surface—the preferred chemistry for linking synthetic oligonucleotides to a surface (see "Comparison between different strategies of covalent attachment of DNA to glass surfaces to build DNA microarrays" by Zammatteo et. al. *Anal. Biochem.*, 280: 143–150 (2000)). This can be accomplished by coating the MicroDisks bearing an —$SiO_2$ surface with 3-glycidoxyproplytrimethoxysilane and hydrolyzing the resulting epoxide to a diol. The diol surface is converted to an aldehyde by periodate oxidation and an amino-tagged synthetic capture oligonucleotide is covalently linked to the surface. Many such encoded MicroDisks, each containing a different capture oligonucleotides, can be made in this manner. Oligonucleotide-containing MicroDisks are then incubated with a sample containing fluorescently-labeled cDNA complementary to the capture oligonucleotide. After a suitable incubation time and washing steps, the MicroDisks are arrayed and subjected to analysis on an optical reader to detect the encoding pattern and on a fluorescence reader to determine the level of bound antigen.

Library Synthesis

In the absence of a device or instrument that can sort individual MicroDisks, library synthesis is random. Using the split and pool method libraries can be synthesized directly onto the MicroDisks. After each step in the synthesis, the MicroDisks are arrayed and optically decoded before proceeding onto the next synthesis cycle. For example in the case of DNA, after the first cycle the disks are mixed and divided into four groups, one group each for A, C, T, and G bases. The four groups are arrayed and optically decoded and the information is stored. The process is then repeated for each cycle. At the end of the synthesis the identity of the oligonucleotide on each MicroDisk is known. In this method of random library synthesis, no two microdevices should have same photorecognizable coding/encoding pattern, because two microdevices with same photorecognizable coding pattern may go through different synthesis cycles and result in different synthesized entities with no method to distinguish between them. In other words, for this example, each microdevice must have a unique photorecognizable coding pattern. On the other hand, in this method of random library synthesis, it is possible for two microdevices having different photorecognizable coding patterns to go through same synthesis cycles, resulting in their having the same synthesized entities. The synthesized libraries can be used for screening. Such a library-synthesis technique could also be used to generate peptide libraries. Any library typically generated on beads could be synthesized on MicroDisks. A very large number of such libraries are known to those practiced in the art of combinatorial chemistry (e.g. "Comprehensive survey of combinatorial library synthesis; 1999" by Dolle *Journal of Combinatorial Chemistry,* 2:383–433 (2000)). This technique requires that each MicroDisk contain a unique code.

A second and more valuable method of library synthesis involves the use of a sorting step after each synthesis cycle. In this method, individually encoded MicroDisks are assigned a target sequence prior to the initiation of library synthesis. After each step in the synthesis, each MicroDisk is directed to the appropriate reaction chamber. Procedure and the specific sequences are preassigned to individual particles. For example, in the case of synthesizing oligonucleotides an encoded MicroDisk assigned the sequence ATCAGTCATGCG (SEQ ID NO:1) would go to the A tube in the first step of synthesis then to the T tube in the second, the C tube in the third, etc. The complete space of the library is determined prior to synthesis and may correspond to a subset of the entire sequence space available e.g., $10^7$ specific 50-residue oligonucleotides out of a sequence space of $10^{30}$, or in the case of peptides, $10^7$ specific 20-residue peptides out of a sequence space of $10^{26}$. In both of these examples, it therefore is possible to generate libraries not available by random synthetic methods (or any methods). Moreover, such techniques can be used to generate genome-specific libraries, e.g., all 50-residue oligonucleotides or all 20-residue peptides present in the human genome. In addition, since the encoded MicroDisks are sorted at each step it is possible to generate multiple copies of the same library in a single synthesis because all MicroDisks containing the same code will be sorted together at each step in the synthesis. For screening purposes, this means that the number of copies of individual MicroDisks can be controlled and more importantly, libraries can be subdivided or mixed with subsets of other libraries to generate new libraries of known sequence.

A major implementation in the synthesis of libraries involves generating a template or scaffold that contains variable regions. Many researchers and companies (e.g. Affibody, Phylos, Ribozyme Pharmaceuticals, Somalogic) have utilized such an approach to generate synthetic antibodies, enzymes, or molecules capable of specific molecular recognition (e.g. aptamers), enzymatic activity (e.g. ribozymes), or signaling (e.g. by fluorescence intensity or fluorescence energy transfer). A common feature of these approaches is that they rely on the use of enzymes (In vitro or Ex vivo) to generate secondary libraries and/or to interpret the results. For example, in the case of aptamer selection, aptamers typically are generated through the SELEX process (Systematic Evolution of Ligands by Exponential enrichments—e.g. U.S. Pat. No. 6,048,698). This involves random synthesis (though flanking regions of specific "template" sequence are required) and then screening to obtain a subpopulation with desired binding properties. This subpopulation is then expanded and randomized by PCR-based methods and screened. This iterative process of expansion and screening is continued until an aptamer of desired specificity and affinity has been generated.

An alternative approach in which screening and expansion are carried out using MicroDisks offers two major advantages. The first is that all requirements that the polymer be amplifiable by an enzymatic process are removed. Consequently, since the polymers in each library iteration can be generated exclusively by chemical synthesis. the polymer can comprise virtually any type or combination of subunits, e.g. nucleotide, amino acid, small organic molecule, sugar, protein-nucleic acid, etc. The tremendously increased diversity of MicroDisk generated libraries enhances the likelihood of being able to produce molecules that carry out particular functions under extremes of condition, e.g. using the molecules in the libraries for capturing proteins under protein-denaturing conditions. Such libraries can be produced using conventional bead based synthesis, but screening and production of further generation libraries becomes rate limiting. In conventional bead-based synthesis, a small subset is identified by analytical methods, e.g. mass spectroscopy, and it is impractical to evaluate the properties of all the members of the library. However, since the identity of each MicroDisk is known though optical decoding, all members of a MicroDisk library can be evaluated. For example, in a library of $10^{10}$ MicroDisks, the binding efficiency of all members of the library can be determined and a subset of sequences can be used as starting points to generate the next generation library. Furthermore, in each library generation information about the measured properties of all library components is retained, facilitating the use of computational approaches to select future generations. Such computational methods benefit greatly from the ability to incorporate conformational constraints into the library, e.g., through the use of specific crosslinks or conformationally constrained subunits. As a result of the huge amount of information obtained during each library screening cycle, using MicroDisk technology the conventional random approach is replaced by a guided systematic one.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A microdevice, which microdevice comprises:
   a) a magnetizable substance;
   b) a photorecognizable coding pattern,
   wherein said microdevice has a preferential axis of magnetization,and wherein an induced magnetization in its absolute magnitude along the preferential axis of the magnetization of said microdevice is at least 20% more than an induced magnetization of said microdevice along at least one other axis, wherein said microdevice has a thin rectangular shape with the preferential axis of the magnetization substantially in the direction of the length of the microdevice, and
  i) wherein said microdevice comprises at least two rectangular structures of said magnetizable substance separated by a non-magnetizable metal layer, and said microdevice has unequal number of said magnetizable substance rectangular structures on each side of said non-magnetizable metal layer along major axis of said microdevice; or
  ii) two rectangular structures of the magnetizable substance along the major axis of the microdevice and at least one of the rectangular structures has fingers on both ends, and
c) a binding partner that is capable of binding to a moiety on a surface of the microdevice.

2. The microdevice of claim 1, wherein the magnetizable substance is selected from the group consisting of a paramagnetic substance, a ferromagnetic substance and a ferrimagnetic substance.

3. The microdevice of claim 1, wherein an induced magnetization in its absolute magnitude along the preferential axis of the magnetization of the microdevice is at least 50%, 75%, or 100% more than an induced magnetization of the microdevice along at least one of any other axes.

4. The microdevice of claim 1, wherein an induced magnetization in its absolute magnitude along the preferential axis of the magnetization of the microdevice is at least one-, two-, five-, ten-, twenty-, or fifty-times more than an induced magnetization of the microdevice along at least one of any other axes.

5. The microdevice of claim 1, wherein the preferential axis of magnetization is substantially aligned with the major axis of the microdevice.

6. The microdevice of claim 1, wherein the magnetizable substance comprises a metal composition.

7. The microdevice of claim 6, wherein the metal composition is a transition metal composition or an alloy thereof.

8. The microdevice of claim 7, wherein the transition metal is selected from the group consisting of iron, nickel, copper, cobalt, manganese, tantalum, zirconium and cobalt-tantalum-zirconium (CoTaZr) alloy.

9. The microdevice of claim 6, wherein the metal composition is $Fe_3O_4$.

10. The microdevice of claim 1, further comprising a non-magnetizable substrate.

11. The microdevice of claim 10, wherein the substrate comprises a material that is selected from the group consisting of silicon, plastic, glass, ceramic, rubber, polymer, silicon dioxide, aluminum oxide, titanium, aluminum, gold and a combination thereof.

12. The microdevice of claim 11, wherein the silicon is silicon dioxide or silicon nitride.

13. The microdevice of claim 1, wherein the substrate comprises a surface that is hydrophobic or hydrophilic.

14. The microdevice of claim 1, wherein the photorecognizable coding pattern is the material composition of the microdevice itself, a structural configuration in the microdevice or an optical labeling substance.

15. The microdevice of claim 14, wherein the versatility of the photorecognizable coding pattern is caused by a shape, number, position distribution, optical refractive property, material composition, or a combination thereof, of or on the microdevice, the structural configuration(s), or the optical labeling substance(s).

16. The microdevice of claim 14, wherein the photorecognizable coding pattern comprises a plurality of the structural configurations and/or a plurality of the optical labeling substances.

17. The microdevice of claim 1, wherein the photorecognizable coding pattern is fabricated or microfabricated on the microdevice.

18. The microdevice of claim 1, wherein the photorecognizable coding pattern is lithographically patterned.

19. The microdevice of claim 18, wherein the lithographical pattern is produced by a method selected from the group consisting of photolithography, electron beam lithography and X-ray lithography.

20. The microdevice of claim 14, wherein the optical labeling substance is deposited on the microdevice.

21. The microdevice of claim 14, wherein the optical labeling substance is located within the microdevice.

22. The microdevice of claim 14, wherein the optical labeling substance is deposited by evaporation or sputtering.

23. The microdevice of claim 14, wherein the optical labeling substance is selected from the group consisting of a fluorescent substance, a scattered-light detectable particle and a quantum dot.

24. The microdevice of claim 23, wherein the quantum dot comprises a Cd—X core, X being Se, S or Te.

25. The microdevice of claim 24, wherein the quantum dot is passivated with an inorganic coating shell.

26. The microdevice of claim 25, wherein the coating shell comprises Y-Z, Y being Cd or Zn, and Z being S or Se.

27. The microdevice of claim 23, wherein the quantum dot comprises a Cd—X core, X being Se, S or Te, or a Y-Z shell, Y being Cd or Zn, and Z being S or Se, and the microdevice is further overcoated with a trialkylphosphine oxide.

28. The microdevice of claim 14, wherein the photorecognizable coding pattern comprises an 1-D and/or a 2-D bar coding pattern.

29. The microdevice of claim 1, wherein the binding partner is an antibody or a nucleotide sequence.

30. The microdevice of claim 1, which comprises a plurality of binding partners on the surface of the microdevice, each binding partner is capable of binding or specifically binding to a different moiety.

31. The microdevice of claim 1, further comprising an element that facilitates and/or enables manipulation of the microdevice and/or a moiety/microdevice complex.

32. The microdevice of claim 31, wherein the element is selected from the group consisting of a conductive material, insulating material, a material having high or low acoustic impedance and a charged material.

33. The microdevice of claim 31, wherein the element facilitates and/or enables manipulation of the microdevice and/or a moiety/microdevice complex by a physical force selected from the group consisting of a dielectrophoresis, a traveling-wave dielectrophoresis, an acoustic, an electrostatic, a mechanical, an optical radiation and a thermal convection force.

34. The microdevice of claim 31, which comprises a plurality of the elements, each of the elements facilitates and/or enables manipulation of the microdevice and/or the moiety/microdevice complex by a different physical force.

35. The microdevice of claim 1, which has a major axis to minor axis ratio of at least about 1.2.

36. The microdevice of claim 1, which comprises at least two rectangular structures of a paramagnetic substance.

37. The microdevice of claim 36, wherein the at least two rectangular structures of the paramagnetic substance are separated by the non-magnetizable metal layer.

38. The microdevice of claim 37, wherein the metal layer comprises aluminum.

39. The microdevice of claim 37, which has unequal number of the paramagnetic substance rectangular structure(s) on each side along the major axis of the microdevice.

40. The microdevice of claim 1, which comprises two rectangular structures of the magnetizable substance along the major axis of the microdevice.

41. The microdevice of claim 40, wherein the two rectangular structures of the paramagnetic substance have fingers on both ends.

42. The microdevice of claim 1, further comprising a functional group suitable for synthesis, conjugation, or binding.

43. The microdevice of claim 42, wherein the functional group is selected from the group consisting of a carboxyl, an amino, a hydroxyl, a sulfhydryl, an epoxy, an ester, an alkene, an alkyne, an alkyl, an aromatic, an aldehyde, a ketone, a sulfate, an amide, an urethane group and a derivative thereof.

44. The microdevice of claim 14, wherein the structural configuration is a hole.

45. The microdevice of claim 36, wherein the at least two rectangular structures of the paramagnetic substance are in the form of strips.

* * * * *